US011980236B2

(12) United States Patent
Aoyama et al.

(10) Patent No.: US 11,980,236 B2
(45) Date of Patent: May 14, 2024

(54) POWER SUPPLY UNIT OF AEROSOL GENERATION DEVICE

(71) Applicant: Japan Tobacco Inc., Tokyo (JP)

(72) Inventors: Tatsunari Aoyama, Tokyo (JP); Hiroshi Kawanago, Tokyo (JP); Toru Nagahama, Tokyo (JP); Takashi Fujiki, Tokyo (JP); Ryo Yoshida, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 18/502,044

(22) Filed: Nov. 5, 2023

(65) Prior Publication Data

US 2024/0074515 A1 Mar. 7, 2024

Related U.S. Application Data

(63) Continuation of application No. PCT/JP2022/008591, filed on Mar. 1, 2022.

(30) Foreign Application Priority Data

May 10, 2021 (JP) ................................ 2021-079911

(51) Int. Cl.
*A24F 13/00* (2006.01)
*A24F 40/20* (2020.01)
(Continued)

(52) U.S. Cl.
CPC .............. *A24F 40/95* (2020.01); *A24F 40/20* (2020.01); *A24F 40/465* (2020.01); *A24F 40/51* (2020.01); *A24F 40/65* (2020.01)

(58) Field of Classification Search
CPC ...................................................... A24F 47/00
(Continued)

(56) References Cited

U.S. PATENT DOCUMENTS 11,076,642 B1 * 8/2021 Fuisz ...................... A24F 40/40
11,582,522 B1 * 2/2023 Mahyar .............. H04N 21/4532
(Continued)

FOREIGN PATENT DOCUMENTS

CN 104348214 A 2/2015
CN 206482013 U 9/2017
(Continued)

OTHER PUBLICATIONS

International Search Report and Written Opinion dated Apr. 19, 2022, received for PCT Application PCT/ JP2022/008591, filed on Mar. 1, 2022, 9 pages including English Translation.
(Continued)

*Primary Examiner* — Phuong K Dinh
(74) *Attorney, Agent, or Firm* — XSENSUS LLP

(57) ABSTRACT

A power supply unit of an aerosol generation device which a heating unit is attachable to and detachable from includes: a secondary battery; a case forming a surface of the power supply unit; a chassis accommodated in an internal space of the case and made of an insulating resin; a plurality of magnets held by the chassis with a gap therebetween; an inner member covering a side surface of the chassis; and an outer member covering an outer surface of the inner member. The inner member includes a plurality of through holes exposing the plurality of magnets, and the outer member is replaceably fixed by the plurality of magnets exposed from the plurality of through holes.

8 Claims, 24 Drawing Sheets

(51) Int. Cl.

*A24F 40/465* (2020.01)
*A24F 40/95* (2020.01)
*A24F 40/51* (2020.01)
*A24F 40/65* (2020.01)

(58) Field of Classification Search

USPC .................................................. 131/328–329

See application file for complete search history.

(56) References Cited

U.S. PATENT DOCUMENTS

| | | | |
|---|---|---|---|
| 2019/0230985 | A1 | 8/2019 | Chan et al. |
| 2020/0229502 | A1 | 7/2020 | Akao |
| 2020/0229503 | A1 | 7/2020 | Akao |
| 2020/0229504 | A1 | 7/2020 | Akao |
| 2020/0229505 | A1 | 7/2020 | Akao |
| 2020/0233444 | A1 | 7/2020 | Akao |
| 2020/0235599 | A1 | 7/2020 | Akao |
| 2020/0235600 | A1 | 7/2020 | Akao |
| 2021/0143658 | A1 | 5/2021 | Akao |
| 2021/0234390 | A1 | 7/2021 | Akao |
| 2021/0242702 | A1 | 8/2021 | Akao |
| 2021/0391737 | A1 | 12/2021 | Akao |
| 2023/0187956 | A1 | 6/2023 | Akao |

FOREIGN PATENT DOCUMENTS

| | | | |
|---|---|---|---|
| CN | 206865186 | U | 1/2018 |
| CN | 110447973 | A | 11/2019 |
| CN | 210747257 | U | 6/2020 |
| JP | 2015-529458 | A | 10/2015 |
| JP | 6633788 | B1 | 1/2020 |
| JP | 2020-114197 | A | 7/2020 |

OTHER PUBLICATIONS

Extended European Search Report dated Aug. 8, 2023, received for EP Application 23184932.4, 10 pages including English Translation.

Decision to Grant dated May 10, 2022, received for JP Application 2022-522300, 5 pages including English Translation.

* cited by examiner

POWER SUPPLY UNIT OF AEROSOL GENERATION DEVICE

CROSS-REFERENCE TO RELATED APPLICATIONS

This application is a continuation of International Patent Application No. PCT/JP2022/008591 filed on Mar. 1, 2022, claiming priority to Japanese Patent Application No. 2021-079911 filed on May 10, 2021, the content of each is incorporated herein by reference.

TECHNICAL FIELD

The present disclosure relates to a power supply unit of an aerosol generation device.

BACKGROUND

In the related art, aerosol generation devices that generate aerosol by heating an aerosol source, add a flavor component to the generated aerosol, and deliver the aerosol containing the flavor component to a user are known.

Generally, a power supply unit of these aerosol generation devices includes a controller configured to control a supply of power from a power supply to a heater. In the power supply unit of these aerosol generation devices, it is desirable that the controller is appropriately protected.

Accordingly, for example, Chinese Utility Model number 206865186 Specification (hereinafter, referred to as Patent Literature 1), Chinese Patent Application Publication number 104348214 Specification (hereinafter, referred to as Patent Literature 2), and Japanese Patent number 6633788 (hereinafter, referred to as Patent Literature 3) disclose a power supply unit of an aerosol generation device including a protection unit that protects a controller when an overvoltage and an overcurrent are input from an external power supply.

However, Patent Literature 1 and Patent Literature 2 do not specifically disclose the protection unit of the controller against external noise such as static electricity in the power supply unit of the aerosol generation device.

SUMMARY

The present disclosure relates to providing a power supply unit of an aerosol generation device that can prevent a controller from malfunctioning or failing due to external noise and that improves durability of the power supply unit of the aerosol generation device.

An aspect of the present disclosure relates to a power supply unit of an aerosol generation device which a heating unit is attachable to and detachable from, including:

- a secondary battery;
- a case forming a surface of the power supply unit;
- a chassis accommodated in an internal space of the case and made of an insulating resin;
- a plurality of magnets held by the chassis with a gap therebetween;
- an inner member covering a side surface of the chassis; and
- an outer member covering an outer surface of the inner member, in which the inner member includes a plurality of through holes exposing the plurality of magnets, and the outer member is replaceably fixed by the plurality of magnets exposed from the plurality of through holes.

DESCRIPTION OF EMBODIMENTS

Hereinafter, a suction system according to an embodiment of an aerosol generation device in the present disclosure will be described with reference to the drawings.

The suction system includes a non-combustion-type inhaler 100 (hereinafter, also simply referred to as "inhaler 100") according to the embodiment of the power supply unit of the present disclosure, and a rod 500 heated by the inhaler 100. In the following description, a configuration in which the inhaler 100 accommodates a heating unit in an unattachable and undetachable manner will be described as an example. However, the heating unit may be configured to be attachable to and detachable from the inhaler 100. For example, a unit in which the rod 500 and the heating unit are integrated may be configured to be attachable to and detachable from the inhaler 100. That is, the power supply unit of the aerosol generation device may be configured not to include the heating unit as a constituent element. The words "unattachable and undetachable" refer to a mode in which detachment cannot be performed as long as application is intended. Alternatively, the heating unit may be configured by cooperation of an induction heating coil provided in the inhaler 100 and a susceptor built in the rod 500.

Figure 1:
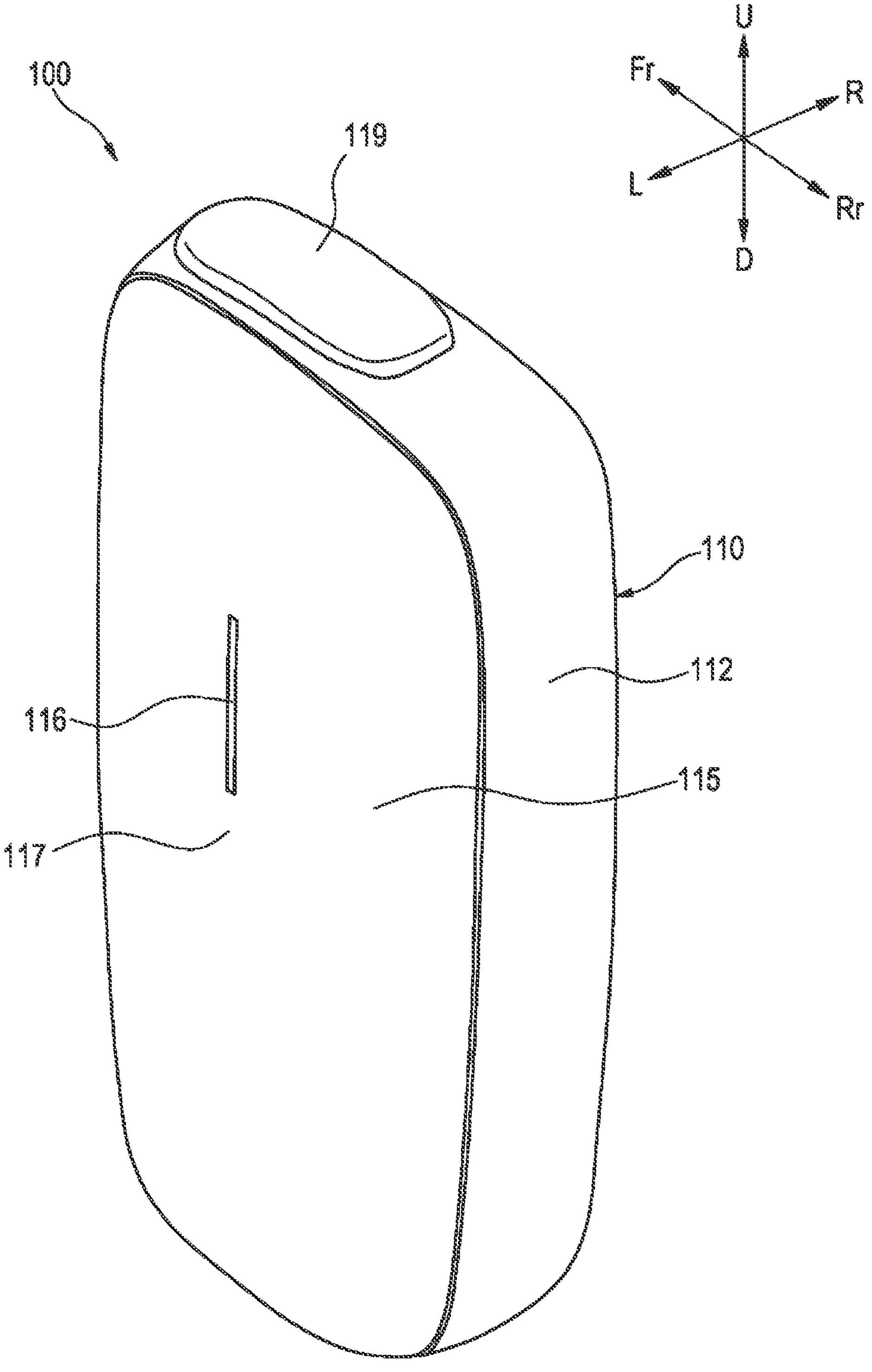
FIG. 1 is a perspective view of a non-combustion-type inhaler.
Figure 2:
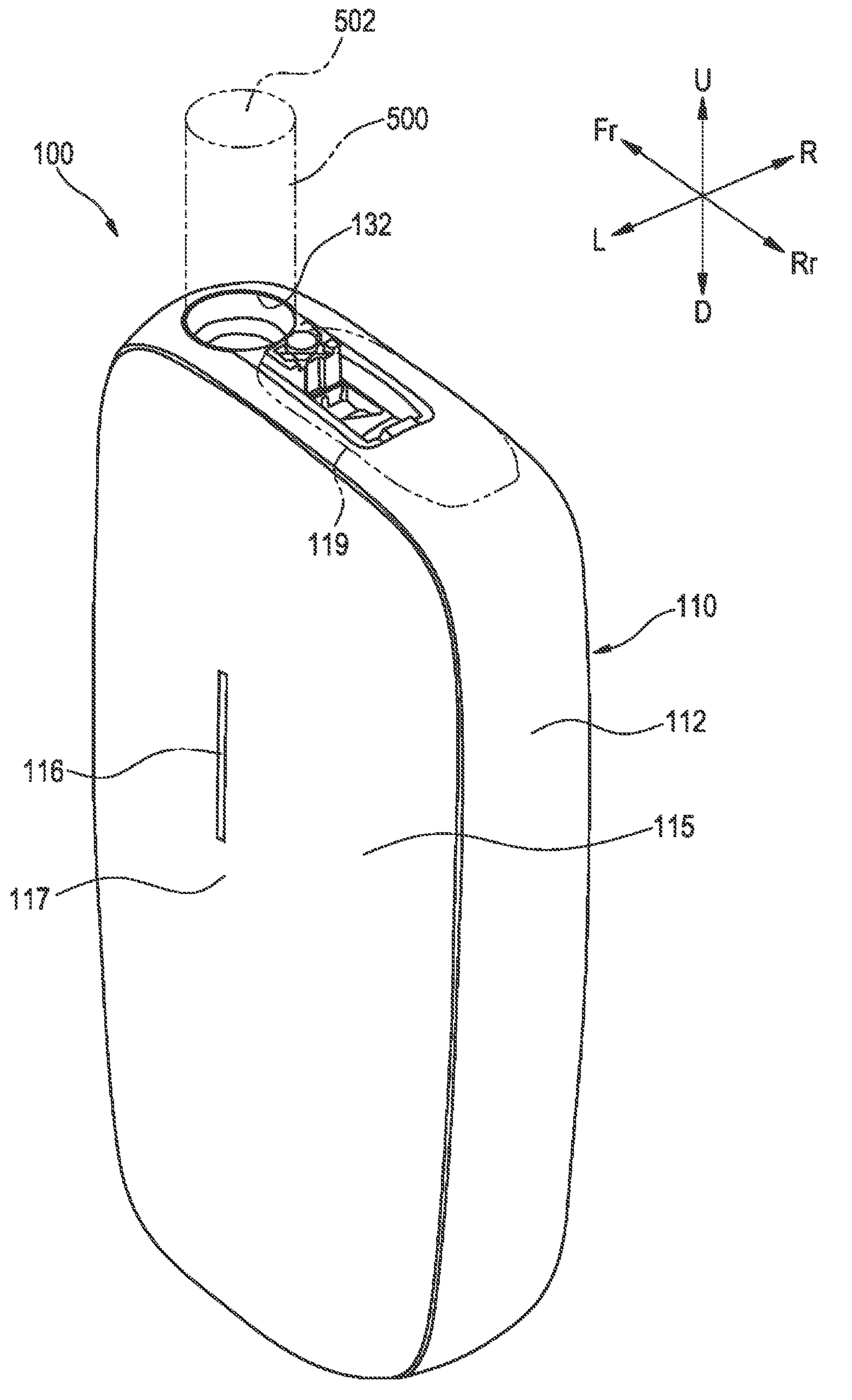
FIG. 2 is a perspective view of the non-combustion-type inhaler showing a state where a rod is attached.
Figure 3:
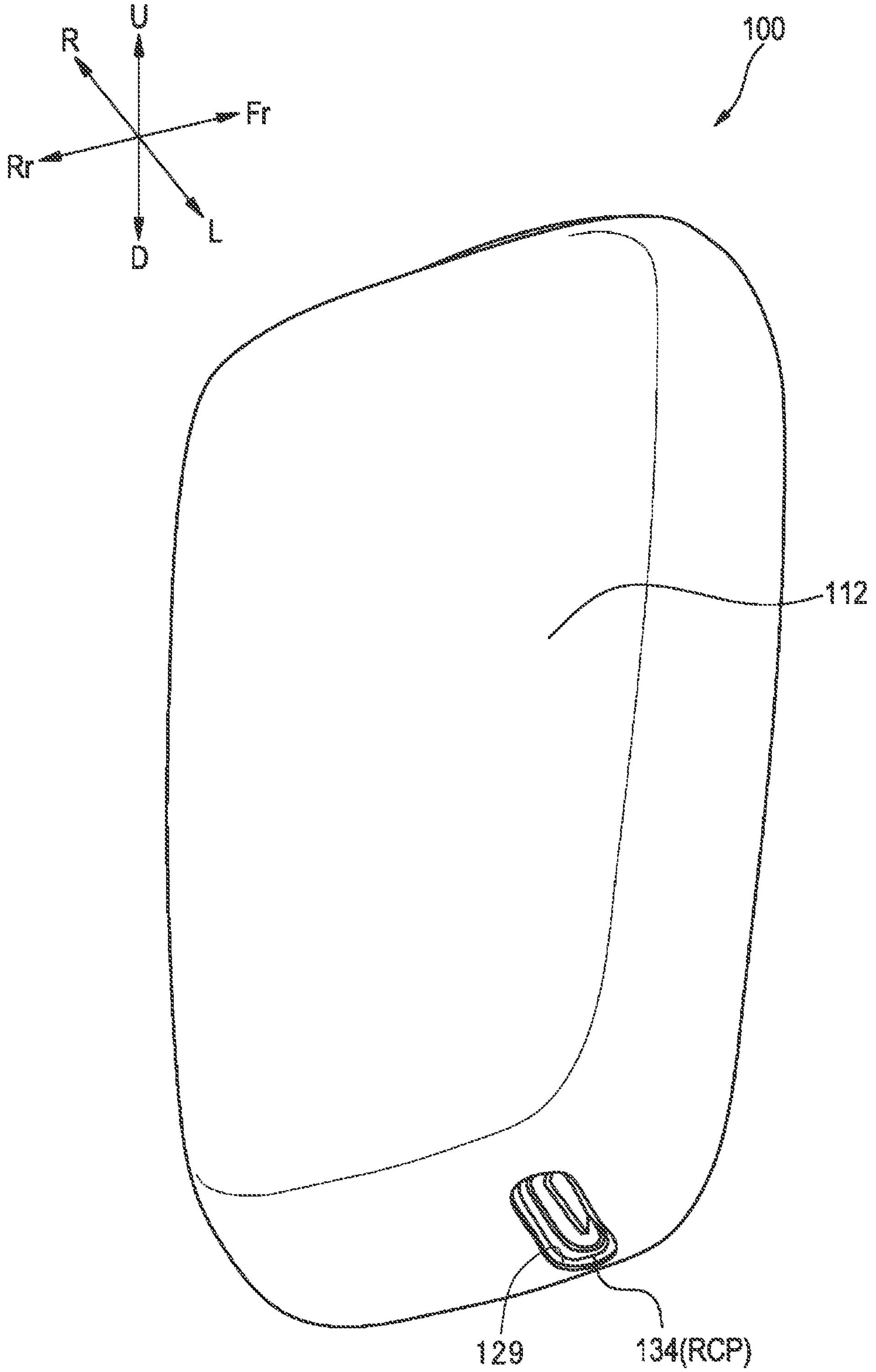
FIG. 3 is another perspective view of the non-combustion-type inhaler.
Figure 4:
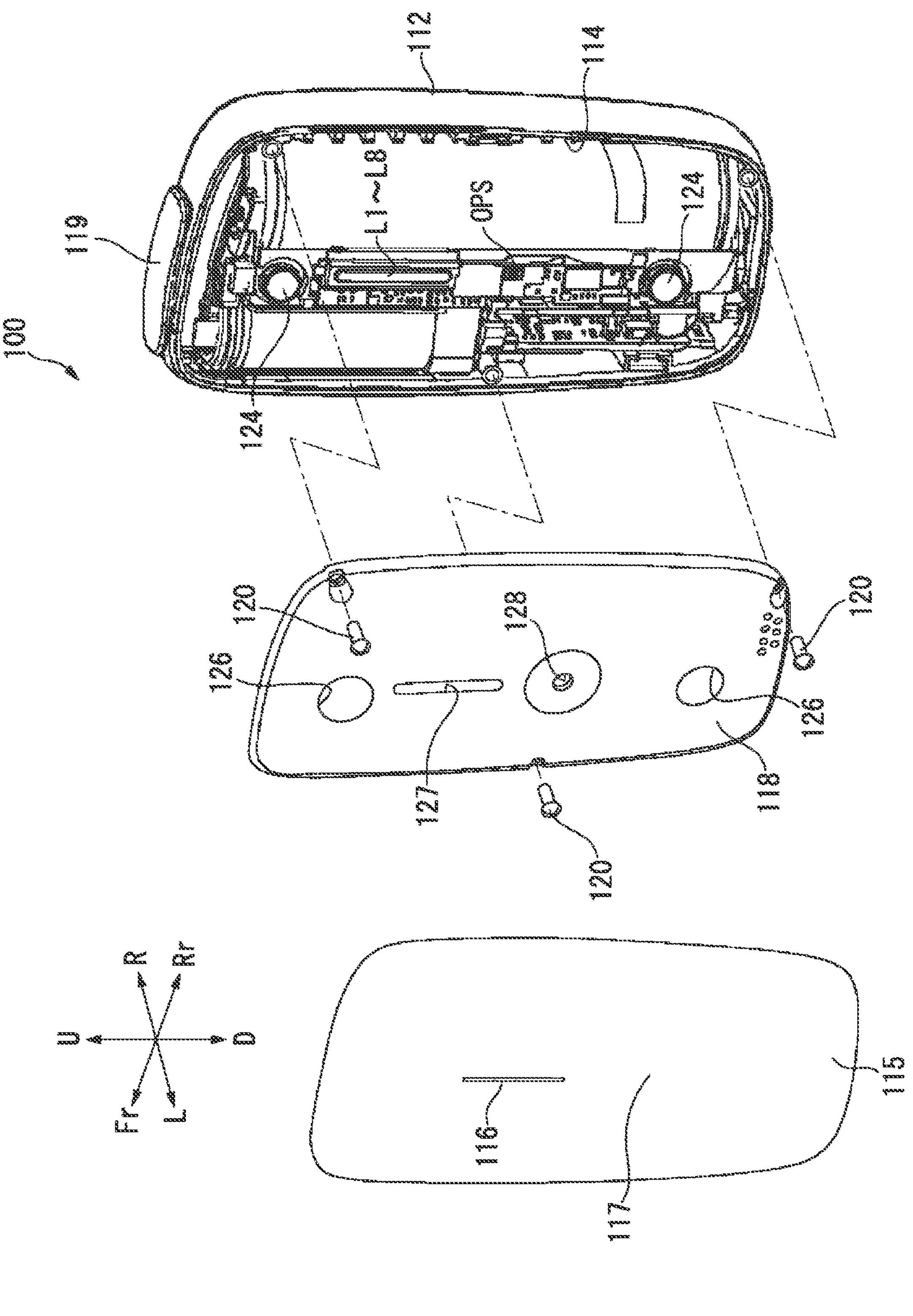
FIG. 4 is an exploded perspective view of the non-combustion-type inhaler.

FIG. 1 is a perspective view showing an overall configuration of the inhaler 100. FIG. 2 is a perspective view of the inhaler 100 showing a state where the rod 500 is attached. FIG. 3 is another perspective view of the inhaler 100. FIG. 4 is an exploded perspective view of the inhaler 100. Further, in the following description, for the sake of convenience, description will be made using an orthogonal coordinate system of a three-dimensional space in which three directions perpendicular to one another are defined as a front-rear direction, a left-right direction, and an upper-lower direction. In the drawings, Fr denotes a front side, Rr denotes a rear side, R denotes a right side, L denotes a left side, U denotes an upper side, and D denotes a lower side.

The inhaler 100 is configured to generate aerosol containing flavor by heating the elongated, substantially cylindrical rod 500 (see FIG. 2) as an example of a flavor component generation base material including a filler containing an aerosol source and a flavor source, and the like.

<Flavor Component Generation Base Material (Rod)>

The rod 500 includes the filler containing the aerosol source heated at a predetermined temperature to generate the aerosol.

A type of the aerosol source is not particularly limited, and extracted substances from various natural products and/or constituent components thereof can be selected according to an application. The aerosol source may be a solid, or may be, for example, a polyhydric alcohol such as glycerin or propylene glycol, or a liquid such as water. The aerosol source may include the flavor source such as a tobacco raw material or an extract derived from the tobacco raw material that releases a flavor component by being heated. Gas to which the flavor component is added is not limited to the aerosol, and for example, invisible steam may be generated.

The filler of the rod 500 may contain cut tobacco as the flavor source. A material of the cut tobacco is not particularly limited, and a known material such as lamina or a middle rib can be used. The filler may contain one kind or two or more kinds of fragrances. A type of the fragrance is not particularly limited, and is preferably menthol from a viewpoint of imparting a good flavor. The flavor source may contain a plant (for example, mint, Chinese medicine, or herbs) other than tobacco. Depending on an application, the rod 500 may not include the flavor source.

<Overall Configuration of Non-Combustion-Type Inhaler>

Next, the overall configuration of the inhaler 100 will be described with reference to FIGS. 1 to 4.

The inhaler 100 includes a substantially rectangular parallelepiped case 110 including a front surface, a rear surface, a left surface, a right surface, an upper surface, and a lower surface. The case 110 includes a bottomed tubular case main body 112 in which a front surface, a rear surface, an upper surface, a lower surface, and a right surface are integrally formed, an outer panel 115 and an inner panel 118 that seal an opening portion 114 (see FIG. 4) of the case main body 112 and form a left surface, and a slider 119.

The inner panel 118 is fixed to the case main body 112 by a bolt 120. The outer panel 115 is fixed to the case main body 112 so as to cover an outer surface of the inner panel 118 by magnets 124 held by an insulating chassis 150 (see FIG. 5) described later and accommodated in the case main body 112. Since the outer panel 115 is fixed by the magnets 124, a user can replace the outer panel 115 in accordance with his or her preference.

The inner panel 118 is provided with two through holes 126 through which the magnets 124 penetrate. In the inner panel 118, a vertically long hole 127 and a circular round hole 128 are further provided between the two through holes 126 arranged in the upper-lower direction. The long hole 127 is for transmitting light emitted from eight light emitting diodes (LEDs) L1 to L8 built in the case main body 112. A button-type operation switch OPS built in the case main body 112 penetrates the round hole 128. That is, the operation switch OPS is disposed in the round hole 128 provided in the inner panel 118. Accordingly, the user can detect the light emitted from the eight LEDs L1 to L8 via an LED window 116 of the outer panel 115. Further, the user can press down the operation switch OPS via a pressing portion 117 of the outer panel 115.

As shown in FIG. 2, an opening 132 into which the rod 500 can be inserted is provided in the upper surface of the case main body 112. The slider 119 is coupled to the case main body 112 so as to be movable in the front-rear direction between a position (see FIG. 1) where the opening 132 is closed and a position (see FIG. 2) where the opening 132 is opened.

The operation switch OPS is used to perform various operations of the inhaler 100. For example, the user operates the operation switch OPS via the pressing portion 117 in a state where the rod 500 is inserted into and attached to the opening 132 as shown in FIG. 2. Accordingly, the rod 500 is heated by a heating unit 170 (see FIG. 5) without being combusted. When the rod 500 is heated, the aerosol is generated from the aerosol source included in the rod 500, and the flavor of the flavor source included in the rod 500 is added to the aerosol. The user can suck the aerosol containing the flavor by holding a suction port 502 of the rod 500 that protrudes from the opening 132 in a mouth and sucking.

As shown in FIG. 3, a charge terminal 134, which is for receiving a power supply by being electrically connected to an external power supply such as an outlet or a mobile battery, is provided in the lower surface of the case main body 112. In the present embodiment, the charge terminal 134 is a universal serial bus (USB) Type-C shaped receptacle, and is not limited thereto. The charge terminal 134 is hereinafter also referred to as a receptacle RCP. A long hole 129 that is long in the left-right direction and penetrates in the upper-lower direction is provided in the lower surface of the case main body 112, and the receptacle RCP is disposed in the long hole 129. Then, a USB Type-C shaped plug can be inserted into and removed from the receptacle RCP through the long hole 129.

The charge terminal 134 may include, for example, a power reception coil, and may be configured to receive power transmitted from the external power supply in a non-contact manner. In this case, a wireless power transfer method may be an electromagnetic induction type, a magnetic resonance type, or a combination of the electromagnetic induction type and the magnetic resonance type. As another example, the charge terminal 134 can be connected to various USB terminals or the like, and may include the power reception coil described above.

The configuration of the inhaler 100 shown in FIGS. 1 to 4 is merely an example. The inhaler 100 can be configured in various forms such that a gas to which the flavor component is imparted is generated from the rod 500 by holding the rod 500 and applying an action such as heating, and a user can suck the generated gas.

<Internal Configuration of Non-Combustion-Type Inhaler>

An internal unit 140 of the inhaler 100 will be described with reference to FIGS. 5 to 9.

Figure 5:
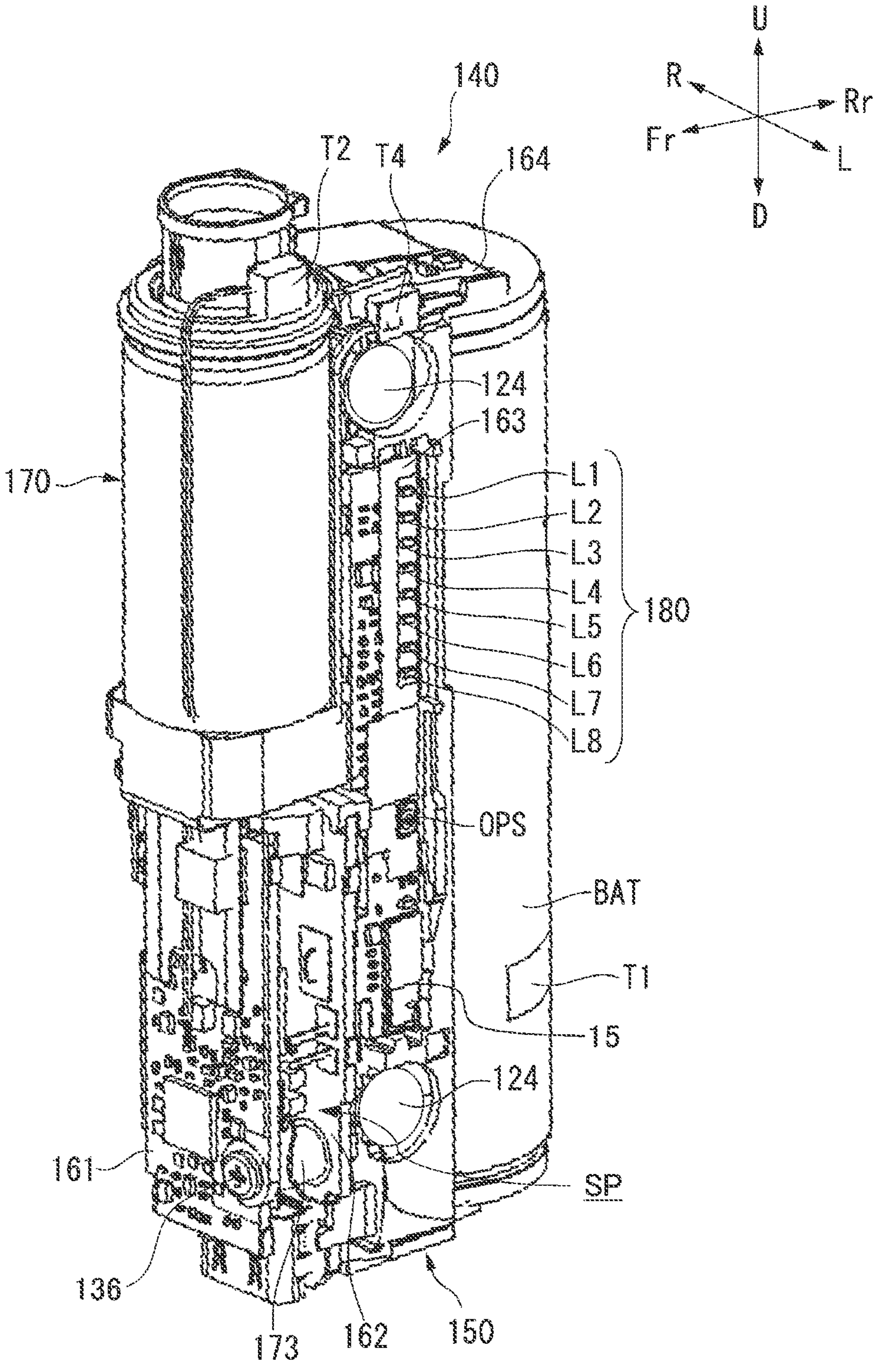
FIG. 5 is a perspective view of an internal unit of the non-combustion-type inhaler.
Figure 6:
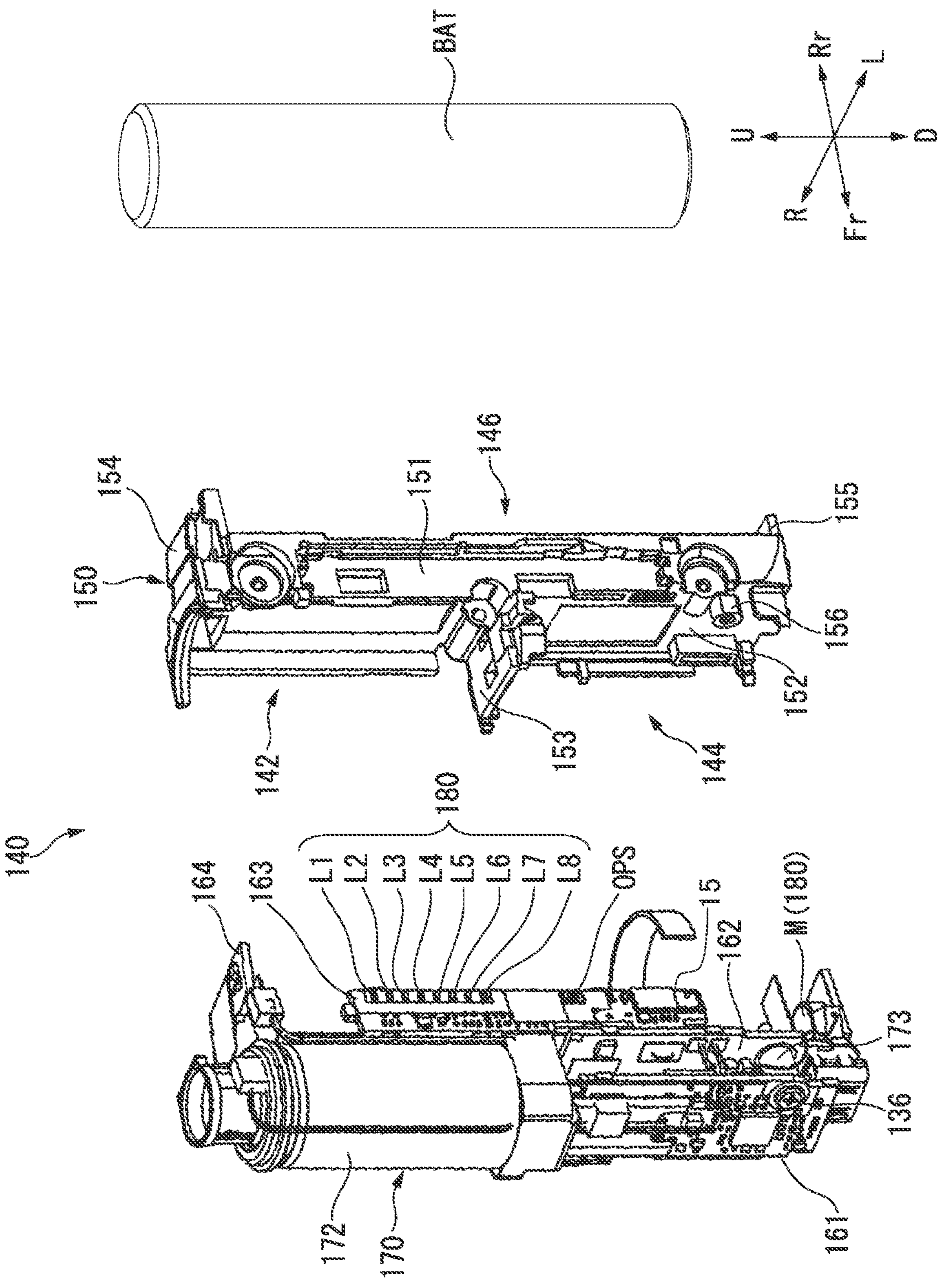
FIG. 6 is an exploded perspective view of the internal unit of FIG. 5.
Figure 7:
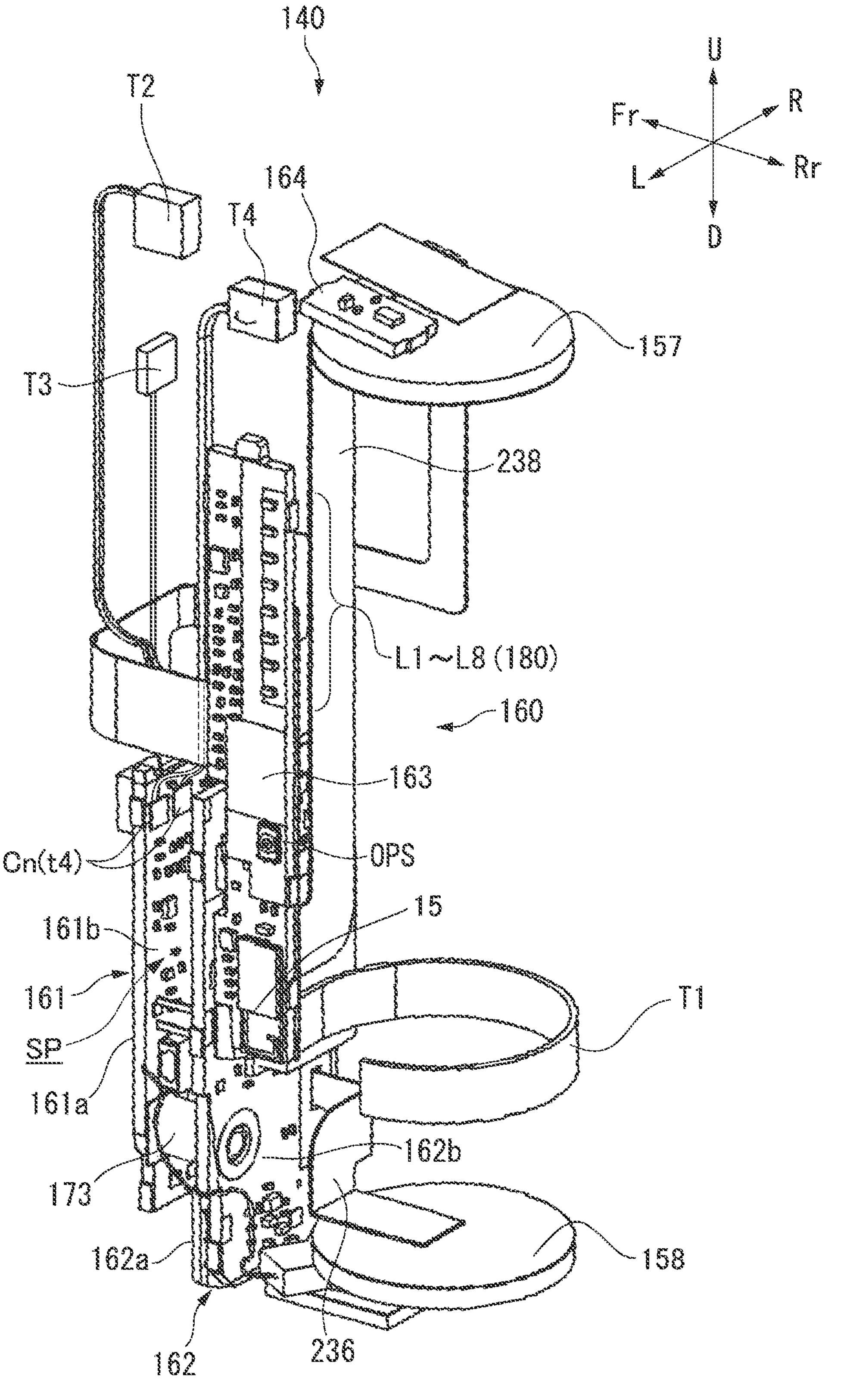
FIG. 7 is a perspective view of the internal unit from which a power supply and a chassis are removed.
Figure 8:
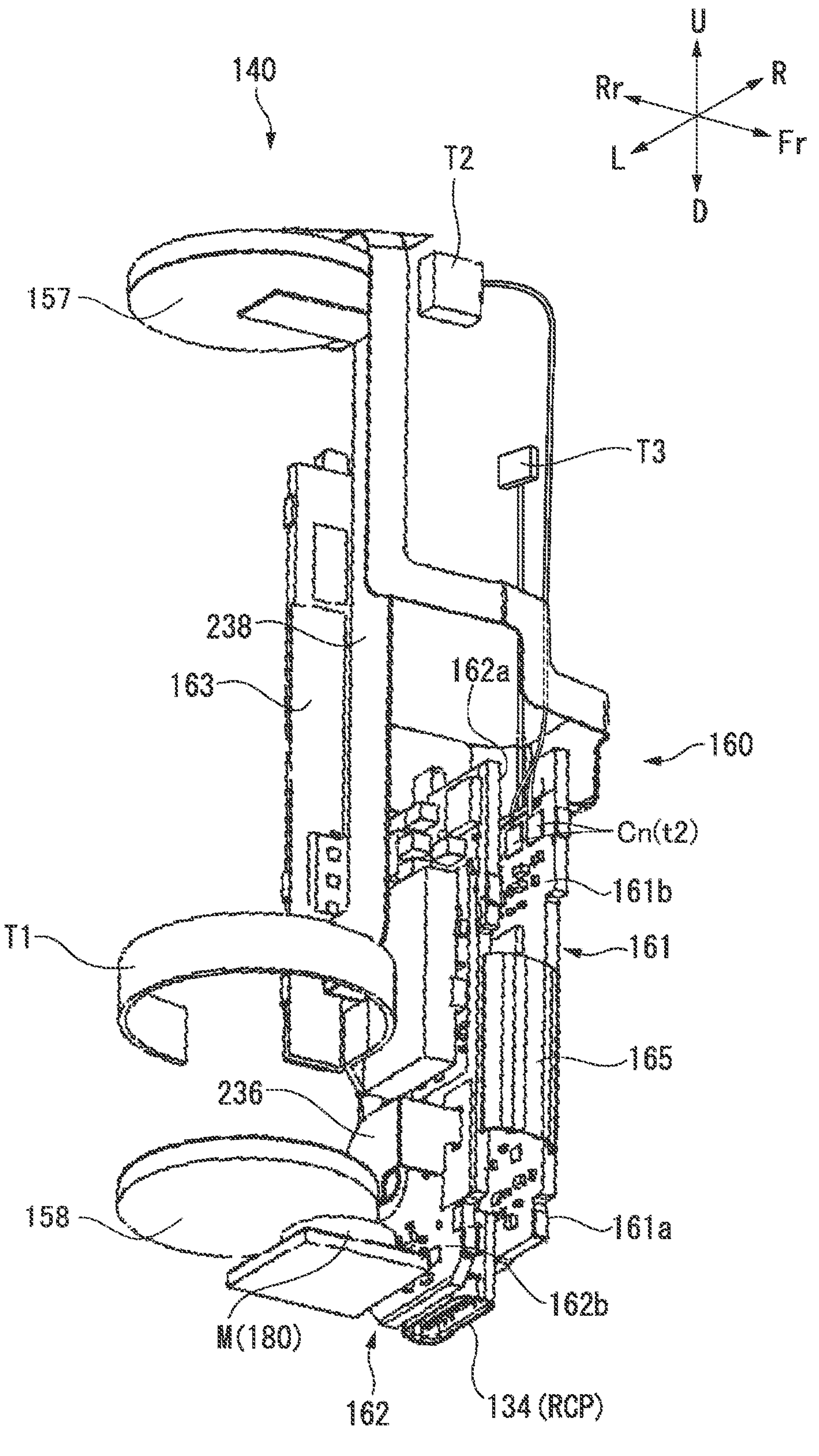
FIG. 8 is another perspective view of the internal unit from which the power supply and the chassis are removed.
Figure 9:
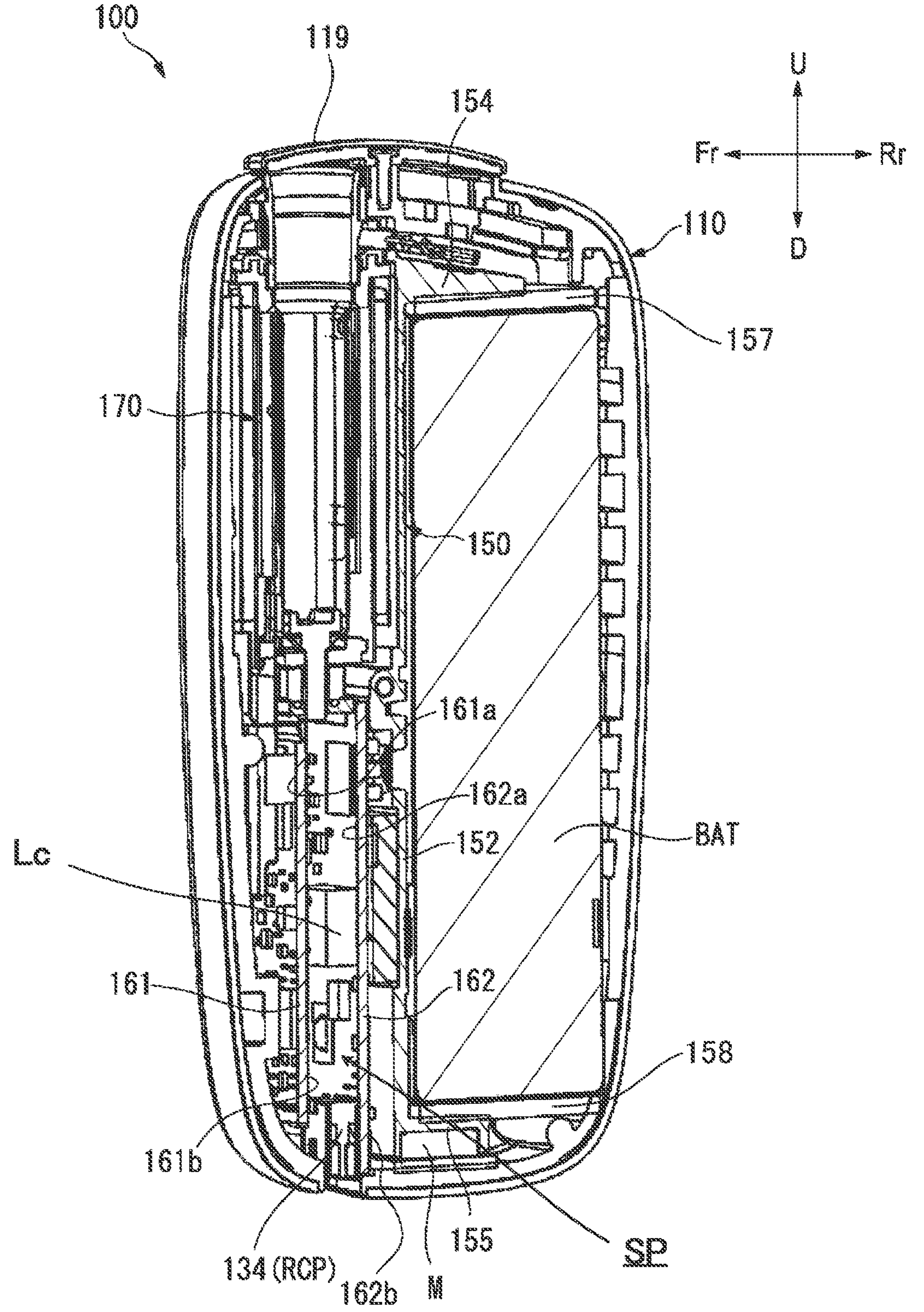
FIG. 9 is a cross-sectional view of the non-combustion-type inhaler.

FIG. 5 is a perspective view of the internal unit 140 of the inhaler 100. FIG. 6 is an exploded perspective view of the internal unit 140 of FIG. 5. FIG. 7 is a perspective view of the internal unit 140 from which a power supply BAT and the chassis 150 are removed. FIG. 8 is another perspective view of the internal unit 140 from which the power supply BAT and the chassis 150 are removed. FIG. 9 is a cross-sectional view of the inhaler 100.

The internal unit 140 accommodated in an internal space of the case 110 includes the chassis 150, the power supply BAT, a circuit unit 160, the heating unit 170, a notification unit 180, and various sensors.

The chassis 150 is made of an insulating material, for example, a resin, which has a property of being resistant to heat. The chassis 150 includes a plate-shaped chassis main body 151 that is disposed substantially at a center of the internal space of the case 110 in the front-rear direction and that extends in the upper-lower direction and the front-rear direction, a plate-shaped front-rear dividing wall 152 that is disposed substantially at the center of the internal space of the case 110 in the front-rear direction and that extends in the upper-lower direction and the left-right direction, a plate-shaped upper-lower dividing wall 153 that extends forward from a substantially center of the front-rear dividing wall 152 in the upper-lower direction, a plate-shaped chassis upper wall 154 that extends rearward from upper edge portions of the front-rear dividing wall 152 and the chassis main body 151, and a plate-shaped chassis lower wall 155 that extends rearward from lower edge portions of the front-rear dividing wall 152 and the chassis main body 151. A left surface of the chassis main body 151 is covered by the inner panel 118 and the outer panel 115 of the case 110 described above.

In the internal space of the case 110, a heating unit accommodation region 142 is defined in a front upper portion by the chassis 150, a board accommodation region 144 is defined in a front lower portion, and a power supply accommodation space 146 is defined in a rear portion along the upper-lower direction.

The heating unit 170 accommodated in the heating unit accommodation region 142 includes a plurality of tubular members, and the plurality of tubular members are concentrically arranged to form a tubular body as a whole. The heating unit 170 includes a rod accommodation portion 172 that can accommodate a part of the rod 500 therein, and a heater HTR (see FIGS. 11 to 20) that heats the rod 500 from an outer periphery or a center. It is preferable that a surface of the rod accommodation portion 172 and the heater HTR are heat-insulated from each other by forming the rod accommodation portion 172 with a heat-insulating material or providing the heat-insulating material inside the rod accommodation portion 172. It is sufficient that the heater HTR is an element that can heat the rod 500. The heater HTR is, for example, a heat generation element. Examples of the heat generation element include a heat generation resistor, a ceramic heater, an induction heating type heater, and the like. As the heater HTR, for example, a heater having a positive temperature coefficient (PTC) characteristic in which a resistance value increases with an increase in a temperature is preferably used. Alternatively, the heater HTR having a negative temperature coefficient (NTC) characteristic in which a resistance value decreases with an increase in a temperature may be used. The heating unit 170 has a function of defining a flow path of air to be supplied to the rod 500 and a function of heating the rod 500. The case 110 has a vent (not shown) for causing the air to flow in, and is configured such that the air can flow into the heating unit 170.

The power supply BAT accommodated in the power supply accommodation space 146 is a rechargeable secondary battery, an electric double layer capacitor, or the like, and is preferably a lithium ion secondary battery. An electrolyte of the power supply BAT may be one of or a combination of a gel-like electrolyte, an electrolytic solution, a solid electrolyte, and an ionic liquid. In the present embodiment, the power supply BAT has a cylindrical shape that extends in the upper-lower direction.

The notification unit 180 notifies various pieces of information such as a state of charge (SOC) indicating a charge state of the power supply BAT, a preheating time during suction, and a suction possible period. The notification unit 180 according to the present embodiment includes the eight LEDs L1 to L8 and a vibration motor M. The notification unit 180 may include a light-emitting element such as the LEDs L1 to L8, may include a vibration element such as the vibration motor M, or may include a sound output element. The notification unit 180 may be a combination of two or more of the light-emitting elements, the vibration element, and the sound output element.

The various sensors include an intake sensor that detects a puff operation (suction operation) of the user, a power supply temperature sensor that detects a temperature of the power supply BAT, a heater temperature sensor that detects a temperature of the heater HTR, a case temperature sensor that detects a temperature of the case 110, a cover position sensor that detects a position of the slider 119, a panel detection sensor that detects attachment and detachment of the outer panel 115, and the like.

The intake sensor mainly includes, for example, a thermistor T2 disposed in the vicinity of the opening 132. The power supply temperature sensor mainly includes, for example, a thermistor T1 disposed in the vicinity of the power supply BAT. The heater temperature sensor mainly includes, for example, a thermistor T3 disposed in the vicinity of the heater HTR. As described above, the rod accommodation portion 172 is preferably heat-insulated from the heater HTR. In this case, the thermistor T3 is preferably in contact with or close to the heater HTR inside the rod accommodation portion 172. When the heater HTR has a PTC characteristic or a NTC characteristic, the heater HTR itself may be used as the heater temperature sensor. The case temperature sensor mainly includes, for example, a thermistor T4 disposed in the vicinity of the left surface of the case 110. The cover position sensor mainly includes a Hall IC 14 including a Hall element disposed in the vicinity of the slider 119. The panel detection sensor mainly includes a Hall IC 13 including a Hall element disposed in the vicinity of an inner surface of the inner panel 118.

The circuit unit 160 includes four circuit boards, a plurality of integrate circuits (ICs), and a plurality of elements. The four circuit boards include an MCU-mounted board 161 on which a micro controller unit (MCU) 1 and a charge IC 2 described later are mainly arranged, a receptacle-mounted board 162 on which the charge terminal 134 is mainly disposed, an LED-mounted board 163 on which the operation switch OPS, the LEDs L1 to L8, and a communication IC 15 described later are arranged, and a Hall IC-mounted board 164 on which the Hall IC 14 described later and including the Hall element that constitutes the cover position sensor is disposed.

The MCU-mounted board 161 and the receptacle-mounted board 162 are arranged parallel to each other in the board accommodation region 144. Specifically, the MCU-mounted board 161 and the receptacle-mounted board 162 are arranged such that respective element arrangement surfaces thereof are arranged along the left-right direction and the upper-lower direction, and the MCU-mounted board 161 is disposed in front of the receptacle-mounted board 162. Each of the MCU-mounted board 161 and the receptacle-mounted board 162 is provided with an opening portion. The MCU-mounted board 161 and the receptacle-mounted board 162 are fastened to a board fixing portion 156 of the front-rear dividing wall 152 by a bolt 136 in a state where a cylindrical spacer 173 is interposed between peripheral edge portions of these opening portions. That is, the spacer 173 fixes positions of the MCU-mounted board 161 and the receptacle-mounted board 162 inside the case 110 together with the chassis 150, and mechanically connects the MCU-mounted board 161 and the receptacle-mounted board 162. Accordingly, it is possible to prevent the MCU-mounted board 161 and the receptacle-mounted board 162 from being in contact with each other and a short-circuit current from being generated therebetween. Further, the spacer 173 may have conductivity, and ground of the MCU-mounted board 161 and ground of the receptacle-mounted board 162 may be connected via the spacer 173.

For the sake of convenience, when surfaces of the MCU-mounted board 161 and the receptacle-mounted board 162 facing forward are respectively set as main surfaces 161*a* and 162*a*, and surfaces opposite to the main surfaces 161*a* and 162*a* are respectively set as secondary surfaces 161*b* and 162*b*, the main surface 161*a* of the MCU-mounted board 161 faces the front surface of the case 110, and the secondary surface 162*b* of the receptacle-mounted board 162 faces the front-rear dividing wall 152 of the chassis 150. The secondary surface 161*b* of the MCU-mounted board 161 and the main surface 162*a* of the receptacle-mounted board 162 face each other with a predetermined gap therebetween. Then, a space SP sandwiched between the MCU-mounted board 161 and the receptacle-mounted board 162 is defined between the secondary surface 161*b* of the MCU-mounted board 161 and the main surface 162*a* of the receptacle-mounted board 162.

The MCU-mounted board 161 and the receptacle-mounted board 162 are electrically connected to each other via a flexible wire board 165.

The LED-mounted board 163 is disposed on a left side surface of the chassis main body 151 and between the two magnets 124 arranged in the upper-lower direction. An element arrangement surface of the LED-mounted board 163 is disposed along the upper-lower direction and the front-rear direction. In other words, element arrangement surfaces of the MCU-mounted board 161 and the receptacle-mounted board 162 are perpendicular to the element arrangement surface of the LED-mounted board 163. In this way, the element arrangement surfaces of the MCU-mounted board 161 and the receptacle-mounted board 162 and the element arrangement surface of the LED-mounted board 163 are not limited to be perpendicular to each other, and preferably intersect with each other (are not parallel to each other).

The vibration motor M that constitutes the notification unit 180 together with the LEDs L1 to L8 is supported by the lower surface of the chassis lower wall 155, and is electrically connected to the MCU-mounted board 161 via a conductive wire. In this way, the vibration motor M is disposed side by side with the power supply BAT in the upper-lower direction in which the power supply BAT extends.

Accordingly, since the vibration motor M and the power supply BAT can be arranged by effectively utilizing the internal space of the case 110 of the inhaler 100, the inhaler 100 can be miniaturized.

An upper cushion member 157 is supported by a lower surface of the chassis upper wall 154, and a lower cushion member 158 is supported by an upper surface of the chassis lower wall 155. The upper cushion member 157 and the lower cushion member 158 are formed of an elastic material such as rubber or foam. The upper cushion member 157 supports an abutment surface of a negative-electrode-side power supply bus bar 238 with respect to a negative electrode terminal of the power supply BAT, and the lower cushion member 158 supports an abutment surface of a positive-electrode-side power supply bus bar 236 with respect to a positive electrode terminal of the power supply BAT.

Then, when the power supply BAT is accommodated in the power supply accommodation space 146, the positive electrode terminal of the power supply BAT abuts against the positive-electrode-side power supply bus bar 236, and the negative electrode terminal of the power supply BAT abuts against the negative-electrode-side power supply bus bar 238. At this time, the upper cushion member 157 is disposed above the power supply BAT, and the lower cushion member 158 is disposed below the power supply BAT. Therefore, when the inhaler 100 receives an impact from an outside, transmission of the impact to the power supply BAT can be alleviated by the upper cushion member 157 and the lower cushion member 158, and the power supply BAT can be protected.

Further, the vibration motor M is disposed on the lower surface of the chassis lower wall 155, the lower cushion member 158 is disposed on the upper surface of the chassis lower wall 155, and the power supply BAT is disposed above the lower cushion member 158. Therefore, the lower cushion member 158 is disposed between the power supply BAT and the vibration motor M in the upper-lower direction.

Accordingly, vibration of the vibration motor M can be prevented from being transmitted to the power supply BAT by the lower cushion member 158, and the vibration of the vibration motor M can be prevented from being transmitted to other electronic components via the power supply BAT. Therefore, it is possible to implement high functionality of the inhaler 100 by the vibration motor M while reducing an influence of the vibration of the vibration motor M on the power supply BAT and the circuit board.

The Hall IC-mounted board 164 is disposed on an upper surface of the chassis upper wall 154.

<Operation Modes of Inhaler>

Figure 10:
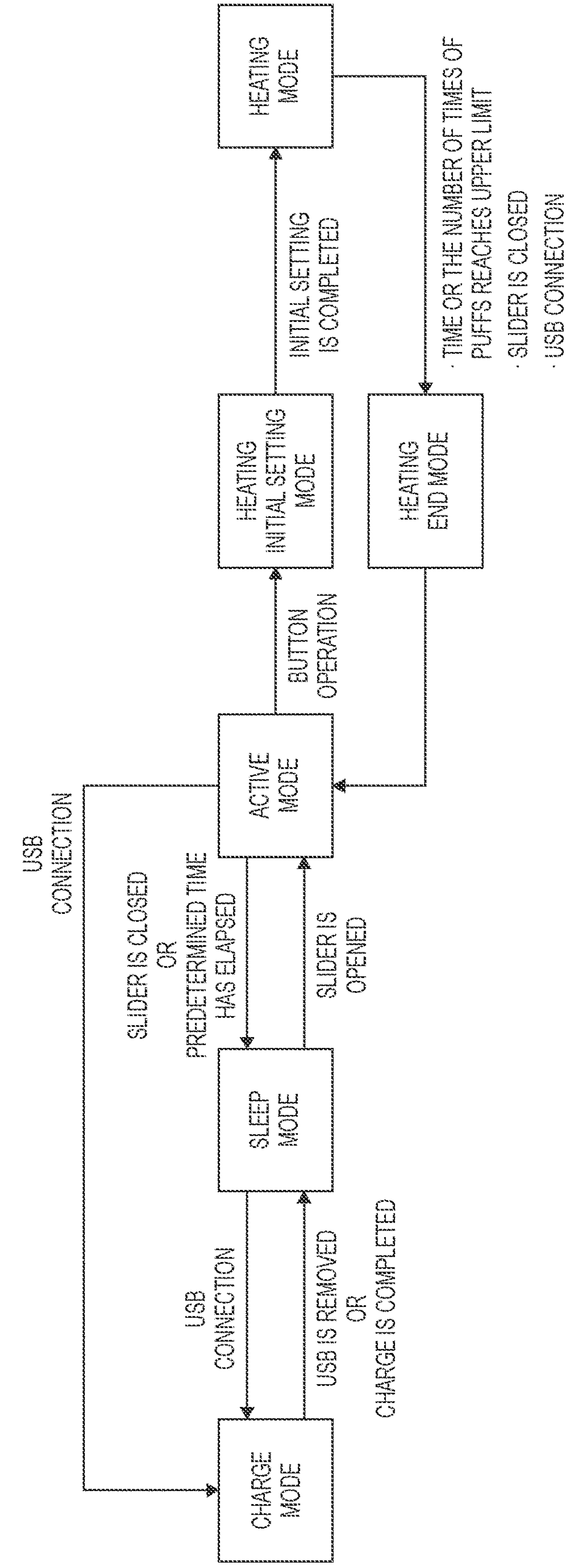
FIG. 10 is a schematic diagram for illustrating operation modes of the inhaler.

FIG. 10 is a schematic diagram for illustrating operation modes of the inhaler 100. As shown in FIG. 10, the operation modes of the inhaler 100 include a charge mode, a sleep mode, an active mode, a heating initial setting mode, a heating mode, and a heating end mode.

The sleep mode is a mode in which power saving is achieved by mainly stopping power supply to electronic components necessary for heating control of the heater HTR.

The active mode is a mode in which most of functions other than the heating control of the heater HTR are enabled. When the slider 119 is opened in a state where the inhaler 100 operates in the sleep mode, the inhaler 100 switches the operation mode to the active mode. When the slider 119 is closed or a non-operation time of the operation switch OPS reaches a predetermined time in a state where the inhaler 100 operates in the active mode, the inhaler 100 switches the operation mode to the sleep mode.

The heating initial setting mode is a mode in which an initial setting of control parameters and the like for starting the heating control of the heater HTR is performed. When an operation of the operation switch OPS is detected in a state where the inhaler 100 operates in the active mode, the inhaler 100 switches the operation mode to the heating initial setting mode, and when the initial setting ends, the inhaler 100 switches the operation mode to the heating mode.

The heating mode is a mode in which the heating control (heating control for aerosol generation and heating control for temperature detection) of the heater HTR is executed. When the operation mode is switched to the heating mode, the inhaler 100 starts the heating control of the heater HTR.

The heating end mode is a mode in which an end processing (a storing processing of a heating history or the like) of the heating control of the heater HTR is executed. When an energization time of the heater HTR or the number of times of suction by the user reaches an upper limit or the slider 119 is closed in a state where the inhaler 100 operates in the heating mode, the inhaler 100 switches the operation mode to the heating end mode, and when the end processing ends, the inhaler 100 switches the operation mode to the active mode. When a USB connection is performed in a state where the inhaler 100 operates in the heating mode, the inhaler 100 switches the operation mode to the heating end mode, and when the end processing ends, the inhaler 100 switches the operation mode to the charge mode. As shown in FIG. 10, in this case, the operation mode may be switched to the active mode before the operation mode is switched to the charge mode. In other words, when the USB connection is performed in a state where the inhaler 100 operates in the heating mode, the inhaler 100 may switch the operation mode in an order of the heating end mode, the active mode, and the charge mode.

The charge mode is a mode in which the power supply BAT is charged by power supplied from an external power supply connected to a receptacle RCP. When the external power supply is connected (USB-connected) to the receptacle RCP in a state where the inhaler 100 operates in the sleep mode or the active mode, the inhaler 100 switches the operation mode to the charge mode. When the charge of the power supply BAT is completed or the connection between the receptacle RCP and the external power supply is released in a state where the inhaler 100 operates in the charge mode, the inhaler 100 switches the operation mode to the sleep mode.

<Outline of Circuit of Internal Unit>

Figure 11:
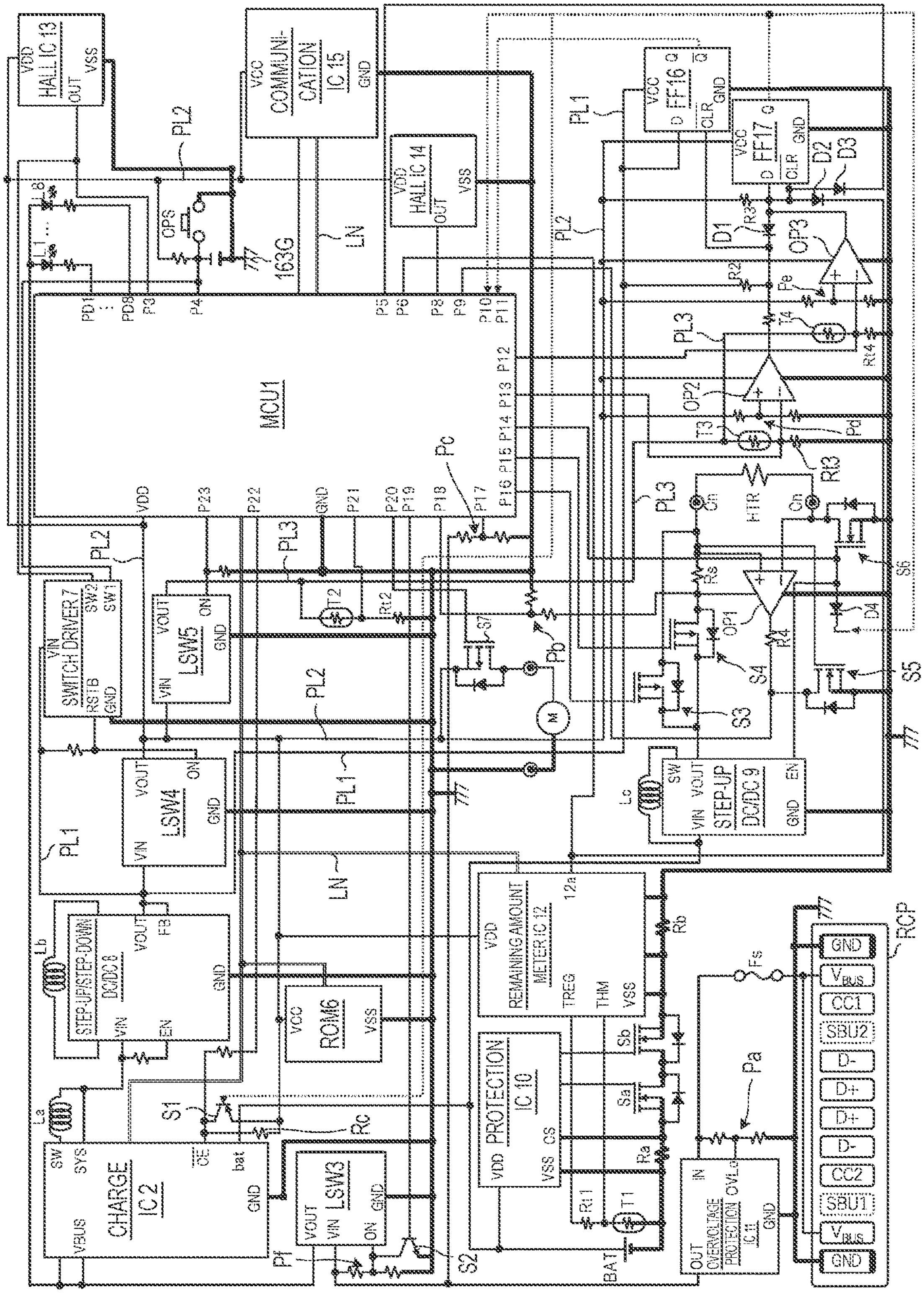
FIG. 11 is a diagram showing a schematic configuration of an electric circuit of the internal unit.
Figure 12:
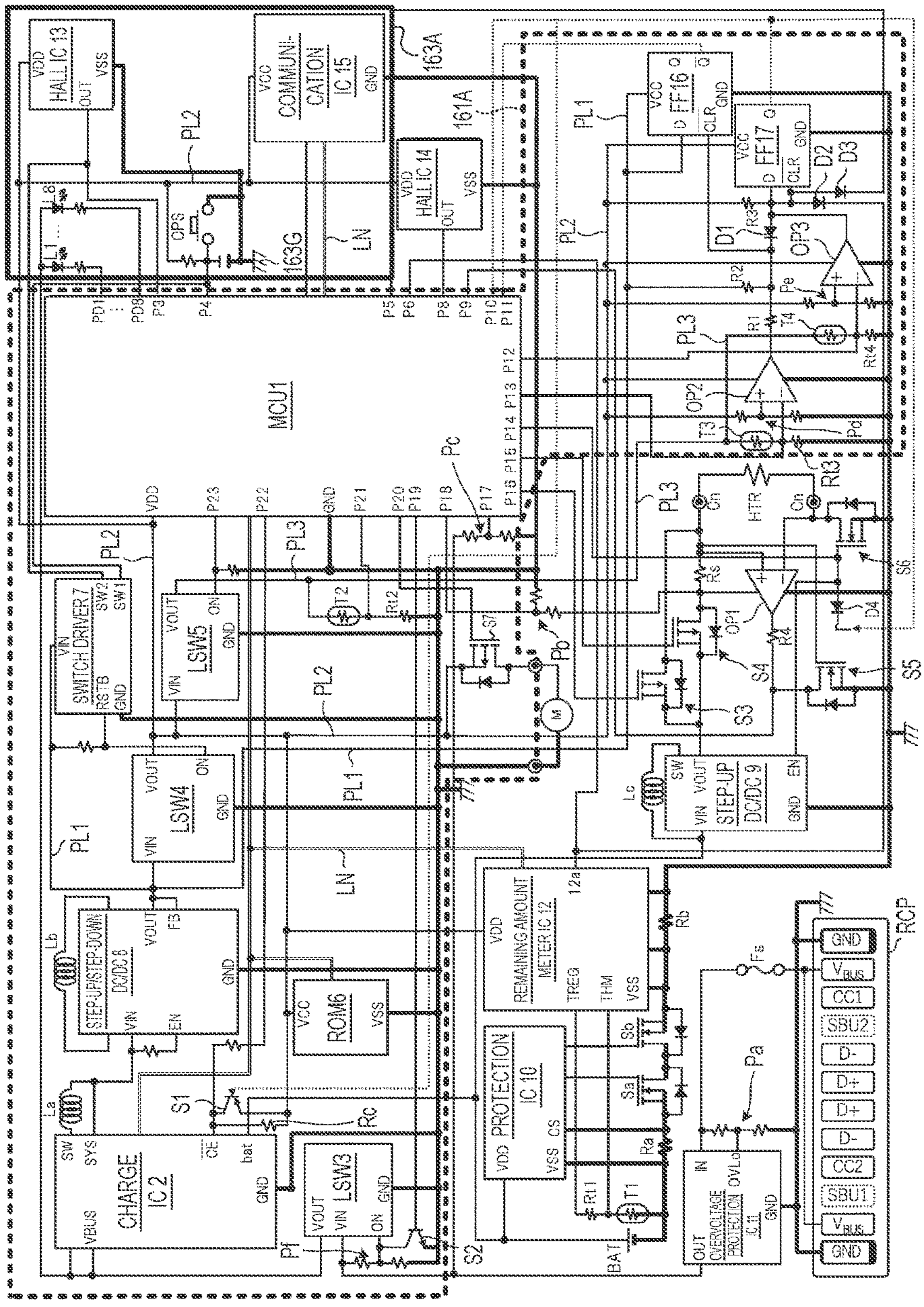
FIG. 12 is a diagram showing a schematic configuration of the electric circuit of the internal unit.
Figure 13:
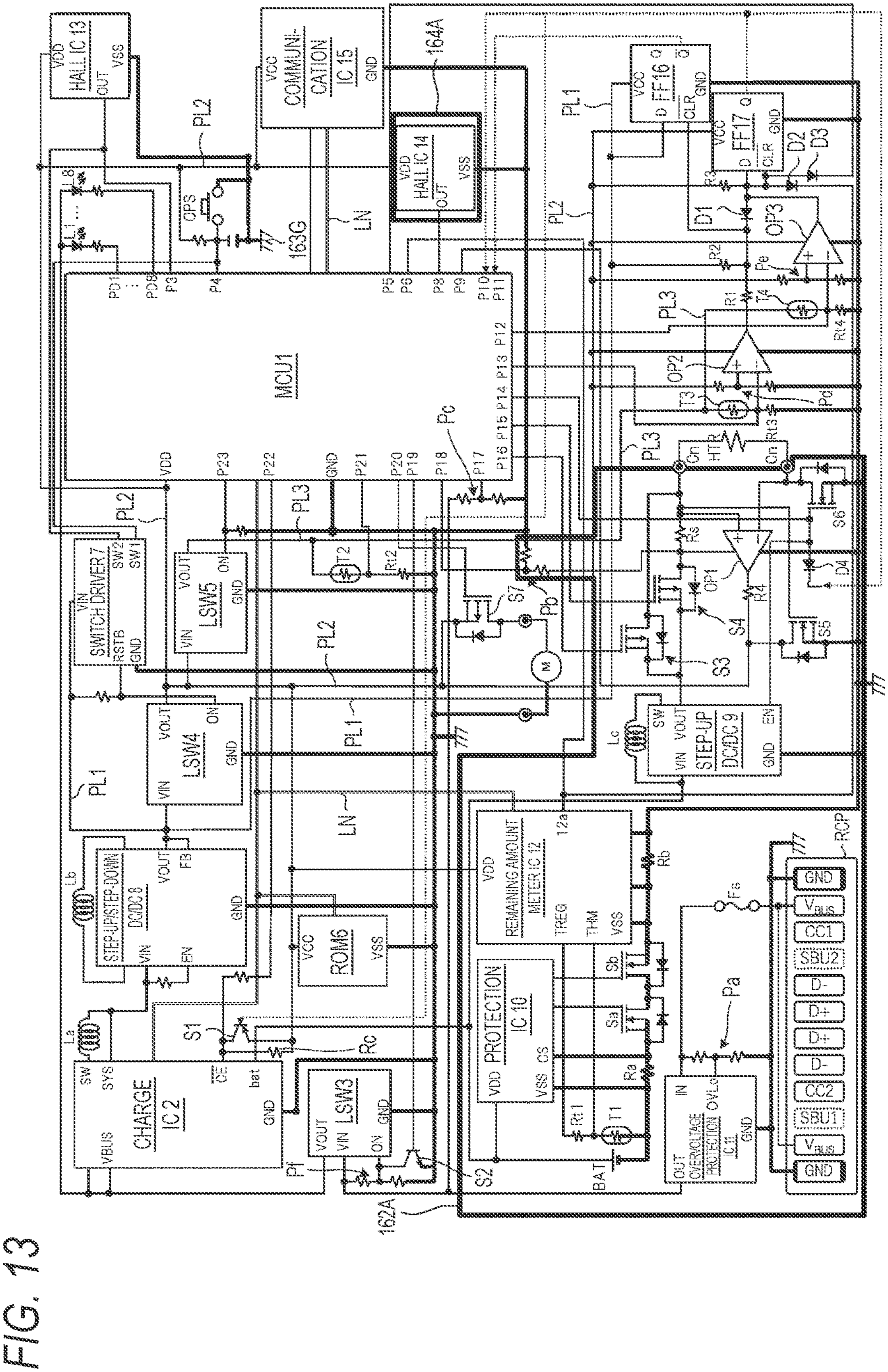
FIG. 13 is a diagram showing a schematic configuration of the electric circuit of the internal unit.

FIGS. 11, 12, and 13 are diagrams showing a schematic configuration of an electric circuit of the internal unit 140. FIG. 12 is the same as FIG. 11 except that a range 161A (a range surrounded by a thick broken line) mounted on the MCU-mounted board 161 and a range 163A (a range surrounded by a thick solid line) mounted on the LED-mounted board 163 are added to the electric circuit shown in FIG. 11. FIG. 13 is the same as FIG. 11 except that a range 162A mounted on the receptacle-mounted board 162 and a range 164A mounted on the Hall IC-mounted board 164 are added to the electric circuit shown in FIG. 11.

A wire indicated by a thick solid line in FIG. 11 is a wire (a wire connected to ground and provided in the internal unit 140) having the same potential as a reference potential (ground potential) of the internal unit 140, and this wire is hereinafter referred to as a ground line. In FIG. 11, an electronic component in which a plurality of circuit elements are formed into a chip is indicated by a rectangle, and reference numerals of various terminals are described inside the rectangle. A power supply terminal VCC and a power supply terminal VDD mounted on the chip indicate power supply terminals on a high potential side. A power supply terminal VSS and a ground terminal GND mounted on the chip indicate power supply terminals on a low potential side (reference potential side). In the electronic component formed into a chip, a difference between a potential of the power supply terminal on the high potential side and a potential of the power supply terminal on the low potential side is a power supply voltage. The electronic component formed into a chip executes various functions by using the power supply voltage.

As shown in FIG. 12, the MCU-mounted board 161 (range 161A) is provided with, as main electronic components, an MCU 1 that performs overall control of the entire inhaler 100, a charge IC 2 that performs charge control of the power supply BAT, load switches (hereinafter, LSWs) 3, 4, and 5 configured by combining a capacitor, a resistor, a transistor, and the like, a read only memory (ROM) 6, a switch driver 7, a step-up/step-down DC/DC converter 8 (referred to as step-up/step-down DC/DC 8 in the drawing), an operational amplifier OP2, an operational amplifier OP3, flip-flops (hereinafter, FF) 16 and 17, a connector Cn (t2) (referred to as a thermistor T2 connected to the connector in the drawing) electrically connected to the thermistor T2 that constitutes the intake sensor, a connector Cn (t3) (referred to as a thermistor T3 connected to the connector in the drawing) electrically connected to the thermistor T3 that constitutes the heater temperature sensor, a connector Cn (t4) (referred to as a thermistor T4 connected to the connector in the drawing) electrically connected to the thermistor T4 that constitutes the case temperature sensor, and a voltage dividing circuit Pc for USB connection detection.

A ground terminal GND of each of the charge IC 2, the LSW 3, the LSW 4, the LSW 5, the switch driver 7, the step-up/step-down DC/DC converter 8, the FF 16, and the FF 17 is connected to the ground line. A power supply terminal VSS of the ROM 6 is connected to the ground line. A negative power supply terminal of each of the operational amplifier OP2 and the operational amplifier OP3 is connected to the ground line.

As shown in FIG. 12, the LED-mounted board 163 (range 163A) is provided with, as main electronic components, a Hall IC 13 including a Hall element that constitutes the panel detection sensor, the LEDs L1 to L8, the operation switch OPS, and a communication IC 15. The communication IC 15 is a communication module for communicating with an electronic device such as a smartphone. Each of a power supply terminal VSS of the Hall IC 13 and a ground terminal GND of the communication IC 15 is connected to the ground line. The communication IC 15 and the MCU 1 can communicate with each other through a communication line LN. One end of the operation switch OPS is connected to ground 163G provided inside the LED-mounted board 163 via the ground line, and the other end of the operation switch OPS is connected to a terminal P4 of the MCU 1.

As shown in FIG. 13, the receptacle-mounted board 162 (range 162A) is provided with, as main electronic components, a power supply connector (referred to as the power supply BAT connected to the power supply connector in the drawing) electrically connected to the power supply BAT, a connector (referred to as the thermistor T1 connected to the connector in the drawing) electrically connected to the thermistor T1 that constitutes the power supply temperature sensor, a step-up DC/DC converter 9 (referred to as step-up DC/DC converter 9 in the drawing), a protection IC 10, an overvoltage protection IC 11, a remaining amount meter IC 12, the receptacle RCP, switches S3 to S6 formed of MOSFETs, the operational amplifier OP1, and a pair of (positive electrode side and negative electrode side) heater connectors Cn electrically connected to the heater HTR.

Two ground terminals GND of the receptacle RCP, a ground terminal GND of the step-up DC/DC converter 9, a power supply terminal VSS of the protection IC 10, a power supply terminal VSS of the remaining amount meter IC 12, a ground terminal GND of the overvoltage protection IC 11, and a negative power supply terminal of the operational amplifier OP1 are connected to the ground line.

As shown in FIG. 13, the Hall IC-mounted board 164 (range 164A) is provided with the Hall IC 14 including the Hall element that constitutes the cover position sensor. A power supply terminal VSS of the Hall IC 14 is connected to the ground line. An output terminal OUT of the Hall IC 14 is connected to a terminal P8 of the MCU 1. The MCU 1 detects opening and closing of the slider 119 based on a signal input to the terminal P8.

As shown in FIG. 12, a connector electrically connected to the vibration motor M is provided on the MCU-mounted board 161.

<Details of Circuit of Internal Unit>

Hereinafter, a connection relationship and the like of electronic components will be described with reference to FIG. 11.

Two power supply input terminals $V_{BUS}$ of the receptacle RCP are connected to an input terminal IN of the overvoltage protection IC 11 via a fuse Fs. When a USB plug is connected to the receptacle RCP and a USB cable including the USB plug is connected to the external power supply, a USB voltage $V_{USB}$ is supplied to the two power supply input terminals $V_{BUS}$ of the receptacle RCP.

One end of a voltage dividing circuit Pa including a series circuit of two resistors is connected to the input terminal IN of the overvoltage protection IC 11. The other end of the voltage dividing circuit Pa is connected to the ground line. A connection point between the two resistors that constitute the voltage dividing circuit Pa is connected to a voltage detection terminal OVLo of the overvoltage protection IC 11. In a state where a voltage input to the voltage detection terminal OVLo is less than a threshold, the overvoltage protection IC 11 outputs a voltage input to the input terminal IN from the output terminal OUT. When the voltage input to the voltage detection terminal OVLo is equal to or higher than the threshold (overvoltage), the overvoltage protection IC 11 protects electronic components downstream of the overvoltage protection IC 11 by stopping a voltage output from the output terminal OUT (cutting off an electrical connection between the LSW 3 and the receptacle RCP). The output terminal OUT of the overvoltage protection IC 11 is connected to an input terminal VIN of the LSW 3 and one end of a voltage dividing circuit Pc (a series circuit of two resistors) connected to the MCU 1. The other end of the voltage dividing circuit Pc is connected to the ground line. A connection point between two resistors that constitute the voltage dividing circuit Pc is connected to a terminal P17 of the MCU 1.

One end of a voltage dividing circuit Pf including a series circuit of two resistors is connected to an input terminal VIN of the LSW 3. The other end of the voltage dividing circuit Pf is connected to the ground line. A connection point between two resistors that constitute the voltage dividing circuit Pf is connected to a control terminal ON of the LSW 3. A collector terminal of a bipolar transistor S2 is connected to the control terminal ON of the LSW 3. An emitter terminal of the bipolar transistor S2 is connected to the ground line. A base terminal of the bipolar transistor S2 is connected to a terminal P19 of the MCU 1. When a signal input to the control terminal ON is a high level, the LSW 3 outputs a voltage input to the input terminal VIN from an output terminal VOUT. The output terminal VOUT of the LSW 3 is connected to an input terminal VBUS of the charge IC 2.

The MCU 1 turns on the bipolar transistor S2 while the USB connection is not performed. Accordingly, since the control terminal ON of the LSW 3 is connected to the ground line via the bipolar transistor S2, a low-level signal is input to the control terminal ON of the LSW 3.

When the USB connection is performed, the bipolar transistor S2 connected to the LSW 3 is turned off by the MCU 1. When the bipolar transistor S2 is turned off, the USB voltage $V_{USB}$ divided by the voltage dividing circuit Pf is input to the control terminal ON of the LSW 3. Therefore, when the USB connection is performed and the bipolar transistor S2 is turned off, a high-level signal is input to the control terminal ON of the LSW 3. Accordingly, the LSW 3 outputs the USB voltage $V_{USB}$ supplied from the USB cable from the output terminal VOUT. Even when the USB connection is performed in a state where the bipolar transistor S2 is not turned off, the control terminal ON of the LSW 3 is connected to the ground line via the bipolar transistor S2. Therefore, it should be noted that a low-level signal continues to be input to the control terminal ON of the LSW 3 unless the MCU 1 turns off the bipolar transistor S2.

The positive electrode terminal of the power supply BAT is connected to a power supply terminal VDD of the protection IC 10, an input terminal VIN of the step-up DC/DC converter 9, and a charge terminal bat of the charge IC 2. Therefore, a power supply voltage $V_{BAT}$ of the power supply BAT is supplied to the protection IC 10, the charge IC 2, and the step-up DC/DC converter 9.

A resistor Ra, a switch Sa formed of a MOSFET, a switch Sb formed of a MOSFET, and a resistor Rb are connected in series in this order to the negative electrode terminal of the power supply BAT. A current detection terminal CS of the protection IC 10 is connected to a connection point between the resistor Ra and the switch Sa. A control terminal of each of the switch Sa and the switch Sb is connected to the protection IC 10. Both ends of the resistor Rb are connected to the remaining amount meter IC 12.

The protection IC 10 acquires a value of a current that flows to the resistor Ra when the power supply BAT is charged and discharged from a voltage input to the current detection terminal CS (a voltage applied to both ends of the resistor Ra), and when the current value becomes excessive (overcurrent), the protection IC 10 performs opening and closing control of the switch Sa and the switch Sb to stop charge or discharge of the power supply BAT, so that the power supply BAT is protected. More specifically, in a case where acquiring the excessive current value when charging the power supply BAT, the protection IC 10 stops charge of the power supply BAT by turning off the switch Sb. In a case where acquiring the excessive current value when discharging the power supply BAT, the protection IC 10 stops discharge of the power supply BAT by turning off the switch Sa. Further, when a voltage value of the power supply BAT is abnormal (in a case of overcharge or overvoltage) from a voltage input to the power supply terminal VDD, the protection IC 10 performs opening and closing control of the switch Sa and the switch Sb to stop charge or discharge of the power supply BAT, so that the power supply BAT is protected. More specifically, when overcharge of the power supply BAT is detected, the protection IC 10 stops charge of the power supply BAT by turning off the switch Sb. When overdischarge of the power supply BAT is detected, the protection IC 10 stops discharge of the power supply BAT by turning off the switch Sa.

A resistor Rt1 is connected to a connector connected to the thermistor T1 disposed in the vicinity of the power supply BAT. A series circuit of the resistor Rt1 and the thermistor T1 is connected to the ground line and a regulator terminal TREG of the remaining amount meter IC 12. A connection point between the thermistor T1 and the resistor Rt1 is connected to a thermistor terminal THM of the remaining amount meter IC 12. The thermistor T1 may be a positive temperature coefficient (PTC) thermistor whose resistance value increases with an increase in a temperature, or may be a negative temperature coefficient (NTC) thermistor whose resistance value decreases with an increase in a temperature.

The remaining amount meter IC 12 detects a current that flows to the resistor Rb, and derives battery information such as a remaining capacity of the power supply BAT, a state of charge (SOC) indicating a charge state, and a state of health (SOH) indicating a normal state based on a detected current value. The remaining amount meter IC 12 supplies a voltage from a built-in regulator connected to the regulator terminal TREG to a voltage dividing circuit of the thermistor T1 and the resistor Rt1. The remaining amount meter IC 12 acquires a voltage divided by the voltage dividing circuit from the thermistor terminal THM, and acquires temperature information on a temperature of the power supply BAT based on the voltage. The remaining amount meter IC 12 is connected to the MCU 1 by the communication line LN for performing serial communication, and is configured to communicate with the MCU 1. The remaining amount meter IC 12 transmits the derived battery information and the acquired temperature information of the power supply BAT to the MCU 1 in response to a request from the MCU 1. The MCU 1 controls discharge from the power supply BAT to the heater HTR based on the remaining capacity of the power supply BAT acquired by the remaining amount meter IC 12. That is, when the remaining capacity of the power supply BAT is equal to or smaller than a predetermined value, the MCU 1 prohibits discharge to the heater HTR and performs a display prompting charge. In order to perform the serial communication, a plurality of signal lines such as a data line for data transmission and a clock line for synchronization are required. It should be noted that only one signal line is shown in FIGS. 11 to 20 for simplification.

The remaining amount meter IC 12 includes a notification terminal 12*a*. The notification terminal 12*a* is connected to a terminal P6 of the MCU 1 and a cathode of a diode D2 described later. When an abnormality such as an excessive temperature of the power supply BAT is detected, the remaining amount meter IC 12 outputs a low-level signal from the notification terminal 12*a* to notify the MCU 1 of occurrence of the abnormality. The low-level signal is also input to a CLR ($\overline{\phantom{x}}$) terminal of the FF 17 via the diode D2.

One end of a reactor Lc is connected to a switching terminal SW of the step-up DC/DC converter 9. The other end of the reactor Lc is connected to the input terminal VIN of the step-up DC/DC converter 9. The step-up DC/DC converter 9 performs on/off control of a built-in transistor connected to the switching terminal SW to perform voltage conversion control of stepping up an input voltage and outputting the stepped-up voltage from the output terminal VOUT. The input terminal VIN of the step-up DC/DC converter 9 is connected to the power supply BAT and constitutes a power supply terminal of the step-up DC/DC converter 9 on a high potential side. When a signal input to an enable terminal EN is at a high level, the step-up DC/DC converter 9 performs a step-up operation. In a USB-connected state, the signal input to the enable terminal EN of the step-up DC/DC converter 9 may be controlled to a low level by the MCU 1. Alternatively, in the USB-connected state, the MCU 1 may not control the signal input to the enable terminal EN of the step-up DC/DC converter 9, so that a potential of the enable terminal EN is made indefinite.

A source terminal of a switch S4 formed of a P-channel type MOSFET is connected to an output terminal VOUT of the step-up DC/DC converter 9. A gate terminal of the switch S4 is connected to a terminal P15 of the MCU 1. One end of a resistor Rs is connected to a drain terminal of the switch S4. The other end of the resistor Rs is connected to the heater connector Cn on a positive electrode side connected to one end of the heater HTR. A voltage dividing circuit Pb including two resistors is connected to a connection point between the switch S4 and the resistor Rs. A connection point between the two resistors that constitute the voltage dividing circuit Pb is connected to a terminal P18 of the MCU 1. The connection point between the switch S4 and the resistor Rs is further connected to a positive power supply terminal of the operational amplifier OP1.

A source terminal of the switch S3 formed of a P-channel type MOSFET is connected to a connection line between the output terminal VOUT of the step-up DC/DC converter 9 and the source terminal of the switch S4. A gate terminal of the switch S3 is connected to a terminal P16 of the MCU 1. A drain terminal of the switch S3 is connected to a connection line between the resistor Rs and the heater connector Cn on the positive electrode side. In this way, a circuit including the switch S3 and a circuit including the switch S4 and the resistor Rs are connected in parallel between the output terminal VOUT of the step-up DC/DC converter 9 and the positive electrode side of the heater connector Cn. Since the circuit including the switch S3 does not include a resistor, the circuit including the switch S3 has a lower resistance than that of the circuit including the switch S4 and the resistor Rs.

A non-inverting input terminal of the operational amplifier OP1 is connected to the connection line between the resistor Rs and the heater connector Cn on the positive electrode side. An inverting input terminal of the operational amplifier OP1 is connected to the heater connector Cn on a negative electrode side connected to the other end of the heater HTR and a drain terminal of the switch S6 formed of an N-channel type MOSFET. A source terminal of the switch S6 is connected to the ground line. A gate terminal of the switch S6 is connected to a terminal P14 of the MCU 1, an anode of a diode D4, and the enable terminal EN of the step-up DC/DC converter 9. A cathode of the diode D4 is connected to a Q terminal of the FF 17. One end of a resistor R4 is connected to an output terminal of the operational amplifier OP1. The other end of the resistor R4 is connected to a terminal P9 of the MCU 1 and a drain terminal of a switch S5 formed of an N-channel type MOSFET. A source terminal of the switch S5 is connected to the ground line. Agate terminal of the switch S5 is connected to a connection line between the resistor Rs and the heater connector Cn on the positive electrode side.

The input terminal VBUS of the charge IC 2 is connected to anodes of the LEDs L1 to L8. That is, the LEDs L1 to L8 are connected in parallel to the input terminal VBUS. Cathodes of the LEDs L1 to L8 are connected to control terminals PD1 to PD8 of the MCU 1 via resistors for current limitation. Transistors (built-in switches) connected to the control terminals PD1 to PD8 and the ground terminal GND are built in the MCU 1.

Therefore, the LEDs L1 to L8 are configured to be operable by the USB voltage $V_{USB}$ supplied from the USB cable connected to the receptacle RCP and a voltage supplied from the power supply BAT via the charge IC 2.

The MCU 1 turns on the built-in switch connected to the control terminal PD1 to energize and turn on the LED L1, and turns off the built-in switch connected to the control terminal PD1 to turn off the LED L1. Since on and off of the built-in switch connected to the control terminal PD1 are switched at a high speed, luminance and light emission pattern of the LED L1 can be dynamically controlled. The LEDs L2 to L8 are also similarly controlled to be turned on by the MCU 1.

The charge IC 2 has a charge function of charging the power supply BAT based on the USB voltage $V_{USB}$ input to the input terminal VBUS. The charge IC 2 acquires a charge current or a charge voltage of the power supply BAT from a terminal or a wire (not shown), and performs charge control of the power supply BAT (power supply control from the charge terminal bat to the power supply BAT) based on the acquired charge current or the charge voltage. Further, the charge IC 2 may acquire temperature information of the power supply BAT transmitted from the remaining amount meter IC 12 to the MCU 1 from the MCU 1 by the serial communication that uses the communication line LN, and may use the temperature information for the charge control.

The charge IC 2 further has a $V_{BAT}$ power path function and an OTG function. The $V_{BAT}$ power path function is a function of outputting, from an output terminal SYS, a system power supply voltage Vcc0 substantially the same as the power supply voltage $V_{BAT}$ input to the charge terminal bat. The OTG function is a function of outputting, from the input terminal VBUS, a system power supply voltage Vcc4 obtained by stepping up the power supply voltage $V_{BAT}$ input to the charge terminal bat. ON/OFF of the OTG function of the charge IC 2 is controlled by the MCU 1 by the serial communication that uses the communication line LN. In the OTG function, the power supply voltage $V_{BAT}$ input to the charge terminal bat may be output from the input terminal VBUS as it is. In this case, the power supply voltage $V_{BAT}$ and the system power supply voltage Vcc4 are substantially the same.

The output terminal SYS of the charge IC 2 is connected to an input terminal VIN of the step-up/step-down DC/DC converter 8. One end of a reactor La is connected to a switching terminal SW of the charge IC 2. The other end of the reactor La is connected to the output terminal SYS of the charge IC 2. A charge enable terminal CE ($\overline{\ \ }$) of the charge IC 2 is connected to a terminal P22 of the MCU 1 via a resistor. Further, a collector terminal of the bipolar transistor S1 is connected to the charge enable terminal CE ($\overline{\ \ }$) of the charge IC 2. An emitter terminal of the bipolar transistor S1 is connected to an output terminal VOUT of an LSW 4 described later. A base terminal of the bipolar transistor S1 is connected to the Q terminal of the FF 17. Further, one end of a resistor Rc is connected to the charge enable terminal CE ($\overline{\ \ }$) of the charge IC 2. The other end of the resistor Rc is connected to the output terminal VOUT of the LSW 4.

A resistor is connected to the input terminal VIN and an enable terminal EN of the step-up/step-down DC/DC converter 8. When the system power supply voltage Vcc0 is input from the output terminal SYS of the charge IC 2 to the input terminal VIN of the step-up/step-down DC/DC converter 8, a signal input to the enable terminal EN of the step-up/step-down DC/DC converter 8 is at a high level, and the step-up/step-down DC/DC converter 8 starts a step-up operation or a step-down operation. The step-up/step-down DC/DC converter 8 generates a system power supply voltage Vcc1 by stepping up or stepping down the system power supply voltage Vcc0 input to the input terminal VIN by switching control of a built-in transistor connected to a reactor Lb, and outputs the generated system power supply voltage Vcc1 from an output terminal VOUT. The output terminal VOUT of the step-up/step-down DC/DC converter 8 is connected to a feedback terminal FB of the step-up/step-down DC/DC converter 8, an input terminal VIN of the LSW 4, an input terminal VIN of the switch driver 7, and a power supply terminal VCC and a D terminal of the FF 16. A wire to which the system power supply voltage Vcc1 output from the output terminal VOUT of the step-up/step-down DC/DC converter 8 is supplied is referred to as a power supply line PL1.

When a signal input to a control terminal ON is at a high level, the LSW 4 outputs the system power supply voltage Vcc1 input to the input terminal VIN from an output terminal VOUT. The control terminal ON of the LSW 4 and the power supply line PL1 are connected via a resistor. Therefore, when the system power supply voltage Vcc1 is supplied to the power supply line PL1, a high-level signal is input to the control terminal ON of the LSW 4. Although a voltage output from the LSW 4 is the same as the system power supply voltage Vcc1 when a wire resistance or the like is ignored, in order to distinguish from the system power supply voltage Vcc1, the voltage output from the output terminal VOUT of the LSW 4 is hereinafter referred to as a system power supply voltage Vcc2.

The output terminal VOUT of the LSW 4 is connected to a power supply terminal VDD of the MCU 1, an input terminal VIN of the LSW 5, a power supply terminal VDD of the remaining amount meter IC 12, a power supply terminal VCC of the ROM 6, the emitter terminal of the bipolar transistor S1, the resistor Rc, and a power supply terminal VCC of the FF 17. A wire to which the system power supply voltage Vcc2 output from the output terminal VOUT of the LSW 4 is supplied is referred to as a power supply line PL2.

When a signal input to a control terminal ON is at a high level, the LSW 5 outputs the system power supply voltage Vcc2 input to an input terminal VIN from an output terminal VOUT. The control terminal ON of the LSW 5 is connected to a terminal P23 of the MCU 1. Although a voltage output from the LSW 5 is the same as the system power supply voltage Vcc2 when a wire resistance or the like is ignored, in order to distinguish from the system power supply voltage Vcc2, the voltage output from the output terminal VOUT of the LSW 5 is hereinafter referred to as a system power supply voltage Vcc3. A wire to which the system power supply voltage Vcc3 output from the output terminal VOUT of the LSW 5 is supplied is referred to as a power supply line PL3.

A series circuit of the thermistor T2 and a resistor Rt2 is connected to the power supply line PL3, and the resistor Rt2 is connected to the ground line. The thermistor T2 and the resistor Rt2 constitute a voltage dividing circuit, and a connection point between the thermistor T2 and the resistor Rt2 is connected to a terminal P21 of the MCU 1. The MCU 1 detects a temperature fluctuation (resistance value fluctuation) of the thermistor T2 based on a voltage input to the terminal P21, and determines presence or absence of a puff operation based on a temperature fluctuation amount thereof.

A series circuit of the thermistor T3 and a resistor Rt3 is connected to the power supply line PL3, and the resistor Rt3 is connected to the ground line. The thermistor T3 and the resistor Rt3 constitute a voltage dividing circuit, and a connection point between the thermistor T3 and the resistor Rt3 is connected to a terminal P13 of the MCU 1 and an inverting input terminal of the operational amplifier OP2. The MCU 1 detects a temperature of the thermistor T3 (corresponding to a temperature of the heater HTR) based on a voltage input to the terminal P13.

A series circuit of the thermistor T4 and a resistor Rt4 is connected to the power supply line PL3, and the resistor Rt4 is connected to the ground line. The thermistor T4 and the resistor Rt4 constitute a voltage dividing circuit, and a connection point between the thermistor T4 and the resistor Rt4 is connected to a terminal P12 of the MCU 1 and an inverting input terminal of the operational amplifier OP3. The MCU 1 detects a temperature of the thermistor T4 (corresponding to a temperature of the case 110) based on a voltage input to the terminal P12.

A source terminal of a switch S7 formed of a MOSFET is connected to the power supply line PL2. A gate terminal of the switch S7 is connected to a terminal P20 of the MCU 1. A drain terminal of the switch S7 is connected to one of a pair of connectors to which the vibration motor M is connected. The other of the pair of connectors is connected to the ground line. The MCU 1 controls opening and closing of the switch S7 by operating potential of a terminal P20, and can cause the vibration motor M to vibrate in a specific pattern. A dedicated driver IC may be used instead of the switch S7.

A positive power supply terminal of the operational amplifier OP2 and a voltage dividing circuit Pd (a series circuit of two resistors) connected to a non-inverting input terminal of the operational amplifier OP2 are connected to the power supply line PL2. A connection point between the two resistors that constitute the voltage dividing circuit Pd is connected to the non-inverting input terminal of the operational amplifier OP2. The operational amplifier OP2 outputs a signal corresponding to a temperature of the heater HTR (a signal corresponding to a resistance value of the thermistor T3). In the present embodiment, since a thermistor having the NTC characteristic is used as the thermistor T3, an output voltage of the operational amplifier OP2 decreases as a temperature of the heater HTR (a temperature of the thermistor T3) increases. This is because a negative power supply terminal of the operational amplifier OP2 is connected to the ground line, and when a voltage value input to the inverting input terminal of the operational amplifier OP2 (a value of a voltage divided by the thermistor T3 and the resistor Rt3) becomes higher than a voltage value input to the non-inverting input terminal of the operational amplifier OP2 (a value of a voltage divided by the voltage dividing circuit Pd), a value of an output voltage of the operational amplifier OP2 becomes substantially equal to a value of a ground potential. That is, when a temperature of the heater HTR (a temperature of the thermistor T3) becomes high, an output voltage of the operational amplifier OP2 is at a low level.

When the thermistor having the PTC characteristic is used as the thermistor T3, an output of the voltage dividing circuit including the thermistor T3 and the resistor Rt3 may be connected to the non-inverting input terminal of the operational amplifier OP2, and an output of the voltage dividing circuit Pd may be connected to the inverting input terminal of the operational amplifier OP2.

A positive power supply terminal of the operational amplifier OP3 and a voltage dividing circuit Pe (a series circuit of two resistors) connected to a non-inverting input terminal of the operational amplifier OP3 are connected to the power supply line PL2. A connection point between the two resistors that constitute the voltage dividing circuit Pe is connected to a non-inverting input terminal of the operational amplifier OP3. The operational amplifier OP3 outputs a signal corresponding to a temperature of the case 110 (a signal corresponding to a resistance value of the thermistor T4). In the present embodiment, since a thermistor having the NTC characteristic is used as the thermistor T4, an output voltage of the operational amplifier OP3 decreases as a temperature of the case 110 increases. This is because a negative power supply terminal of the operational amplifier OP3 is connected to the ground line, and when a voltage value input to the inverting input terminal of the operational amplifier OP3 (a value of a voltage divided by the thermistor T4 and the resistor Rt4) becomes higher than a voltage value input to the non-inverting input terminal of the operational amplifier OP3 (a value of a voltage divided by the voltage dividing circuit Pe), a value of an output voltage of the operational amplifier OP3 becomes substantially equal to a value of the ground potential. That is, when a temperature of the thermistor T4 becomes high, an output voltage of the operational amplifier OP3 is at a low level.

When a thermistor having the PTC characteristic is used as the thermistor T4, an output of the voltage dividing circuit including the thermistor T4 and the resistor Rt4 may be connected to the non-inverting input terminal of the operational amplifier OP3, and an output of the voltage dividing circuit Pe may be connected to the inverting input terminal of the operational amplifier OP3.

A resistor R1 is connected to an output terminal of the operational amplifier OP2. A cathode of a diode D1 is connected to the resistor R1. An anode of the diode D1 is connected to an output terminal of the operational amplifier OP3, a D terminal of the FF 17, and the CLR (—) terminal of the FF 17. A resistor R2 connected to the power supply line PL1 is connected to a connection line between the resistor R1 and the diode D1. Further, a CLR (—) terminal of the FF 16 is connected to the connection line.

One end of a resistor R3 is connected to a connection line between a connection point of the anode of the diode D1 and the output terminal of the operational amplifier OP3 and the D terminal of the FF 17. The other end of the resistor R3 is connected to the power supply line PL2. Further, an anode of a diode D2 connected to the notification terminal 12*a* of the remaining amount meter IC 12, an anode of a diode D3, and the CLR (—) terminal of the FF 17 are connected to the connection line. A cathode of the diode D3 is connected to a terminal P5 of the MCU 1.

When a temperature of the heater HTR becomes excessive, a signal output from the operational amplifier OP2 becomes small, and a signal input to the CLR (—) terminal is at a low level, the FF 16 inputs a high-level signal from a Q (—) terminal to a terminal P11 of the MCU 1. The high-level system power supply voltage Vcc1 is supplied from the power supply line PL1 to a D terminal of the FF 16. Therefore, in the FF 16, a low-level signal continues to be output from the Q (—) terminal unless a signal input to the CLR (—) terminal that operates with negative logic is at a low level.

A signal input to the CLR (—) terminal of the FF 17 is at a low level in any one of a case where a temperature of the heater HTR is excessive, a case where a temperature of the case 110 is excessive, and a case where a low-level signal indicating abnormality detection is output from the notification terminal 12*a* of the remaining amount meter IC 12. When a signal input to the CLR (—) terminal is at a low level, the FF 17 outputs a low-level signal from the Q terminal. The low-level signal is input to a terminal P10 of the MCU 1, the gate terminal of the switch S6, the enable terminal EN of the step-up DC/DC converter 9, and the base terminal of the bipolar transistor S1 connected to the charge IC 2. When a low-level signal is input to the gate terminal of the switch S6, since a gate-source voltage of a N-channel type MOSFET that constitutes the switch S6 is less than a threshold voltage, the switch S6 is turned off. When a low-level signal is input to the enable terminal EN of the step-up DC/DC converter 9, since the enable terminal EN of the step-up DC/DC converter 9 has a positive logic, a step-up operation is stopped. When a low-level signal is input to the base terminal of the bipolar transistor S1, the bipolar transistor S1 is turned on (an amplified current is output from the collector terminal). When the bipolar transistor S1 is turned on, the high-level system power supply voltage Vcc2 is input to a CE (—) terminal of the charge IC 2 via the bipolar transistor S1. Since the CE (—) terminal of the charge IC 2 has a negative logic, charge of the power supply BAT is stopped. Accordingly, heating of the heater HTR and charge of the power supply BAT are stopped. Even when the MCU 1 tries to output a low-level enable signal from the terminal P22 to the charge enable terminal CE (—) of the charge IC 2, when the bipolar transistor S1 is turned on, the amplified current is input from the collector terminal to the terminal P22 of the MCU 1 and the charge enable terminal CE (—) of the charge IC 2. Accordingly, it should be noted that a high-level signal is input to the charge enable terminal CE (—) of the charge IC 2.

The high-level system power supply voltage Vcc2 is supplied from the power supply line PL2 to the D terminal of the FF 17. Therefore, in the FF 17, unless a signal input to the CLR (—) terminal that operates with the negative logic is at a low level, a high-level signal continues to be output from the Q terminal. When a low-level signal is output from the output terminal of the operational amplifier OP3, the low-level signal is input to the CLR (—) terminal of the FF 17 regardless of a level of a signal output from the output terminal of the operational amplifier OP2. It should be noted that when a high-level signal is output from the output terminal of the operational amplifier OP2, the low-level signal output from the output terminal of the operational amplifier OP3 is not influenced by the high-level signal by the diode D1. Further, when a low-level signal is output from the output terminal of the operational amplifier OP2, even when a high-level signal is output from the output terminal of the operational amplifier OP3, the high-level signal is replaced with a low-level signal via the diode D1.

The power supply line PL2 further branches from the MCU-mounted board 161 toward a LED-mounted board 163 and Hall IC-mounted board 164 side. A power supply terminal VDD of the Hall IC 13, a power supply terminal VCC of the communication IC 15, and a power supply terminal VDD of the Hall IC 14 are connected to the power supply line PL2 that branches.

An output terminal OUT of the Hall IC 13 is connected to a terminal P3 of the MCU 1 and a terminal SW2 of the switch driver 7. When the outer panel 115 is detached, a low-level signal is output from the output terminal OUT of the Hall IC 13. The MCU 1 determines whether the outer panel 115 is attached based on a signal input to the terminal P3.

The LED-mounted board 163 is provided with a series circuit (a series circuit of a resistor and a capacitor) connected to the operation switch OPS. The series circuit is connected to the power supply line PL2. A connection point between the resistor and the capacitor of the series circuit is connected to the terminal P4 of the MCU 1, the operation switch OPS, and a terminal SW1 of the switch driver 7. In a state where the operation switch OPS is not pressed, the operation switch OPS is not conducted, and signals input to the terminal P4 of the MCU 1 and the terminal SW1 of the switch driver 7 are at a high level by the system power supply voltage Vcc2. When the operation switch OPS is pressed and the operation switch OPS is in a conductive state, the signals input to the terminal P4 of the MCU 1 and the terminal SW1 of the switch driver 7 are connected to the ground 163G and therefore is at a low level. The MCU 1 detects an operation of the operation switch OPS based on a signal input to the terminal P4.

When the operation switch OPS is pressed by the user, external noise such as static electricity is likely to enter the internal unit 140, but when the operation switch OPS is pressed by the user, the operation switch OPS is connected to the ground 163G. Accordingly, when the operation switch OPS is pressed by the user, even when the external noise enters the internal unit 140 from the operation switch OPS, the external noise can be released to the ground 163G, and therefore durability of the inhaler 100 is improved.

Further, as described above, since the ground 163G is provided inside the LED-mounted board 163, even when the external noise enters the internal unit 140 from the operation switch OPS when the operation switch OPS is pressed by the user, the external noise that enters the internal unit 140 from the operation switch OPS can be prevented from entering a circuit board other than the LED-mounted board 163. Accordingly, an electronic component mounted on a circuit board other than the LED-mounted board 163 can be prevented from failing due to the external noise, and durability of the inhaler 100 is improved.

The switch driver 7 is provided with a reset input terminal RSTB. The reset input terminal RSTB is connected to the control terminal ON of the LSW 4. When levels of signals input to the terminal SW1 and the terminal SW2 are both low (in a state where the outer panel 115 is removed and the operation switch OPS is pressed), the switch driver 7 stops an output operation of the LSW4 by outputting a low level signal from the reset input terminal RSTB. That is, when the operation switch OPS, which is originally pressed down via the pressing portion 117 of the outer panel 115, is directly pressed down by the user in a state where the outer panel 115 is detached, the levels of the signals input to the terminal SW1 and the terminal SW2 of the switch driver 7 are both low.

<Operation of Each Operation Mode of Inhaler>

Hereinafter, an operation of the electric circuit shown in FIG. 11 will be described with reference to FIGS. 14 to 20.

Figure 14:
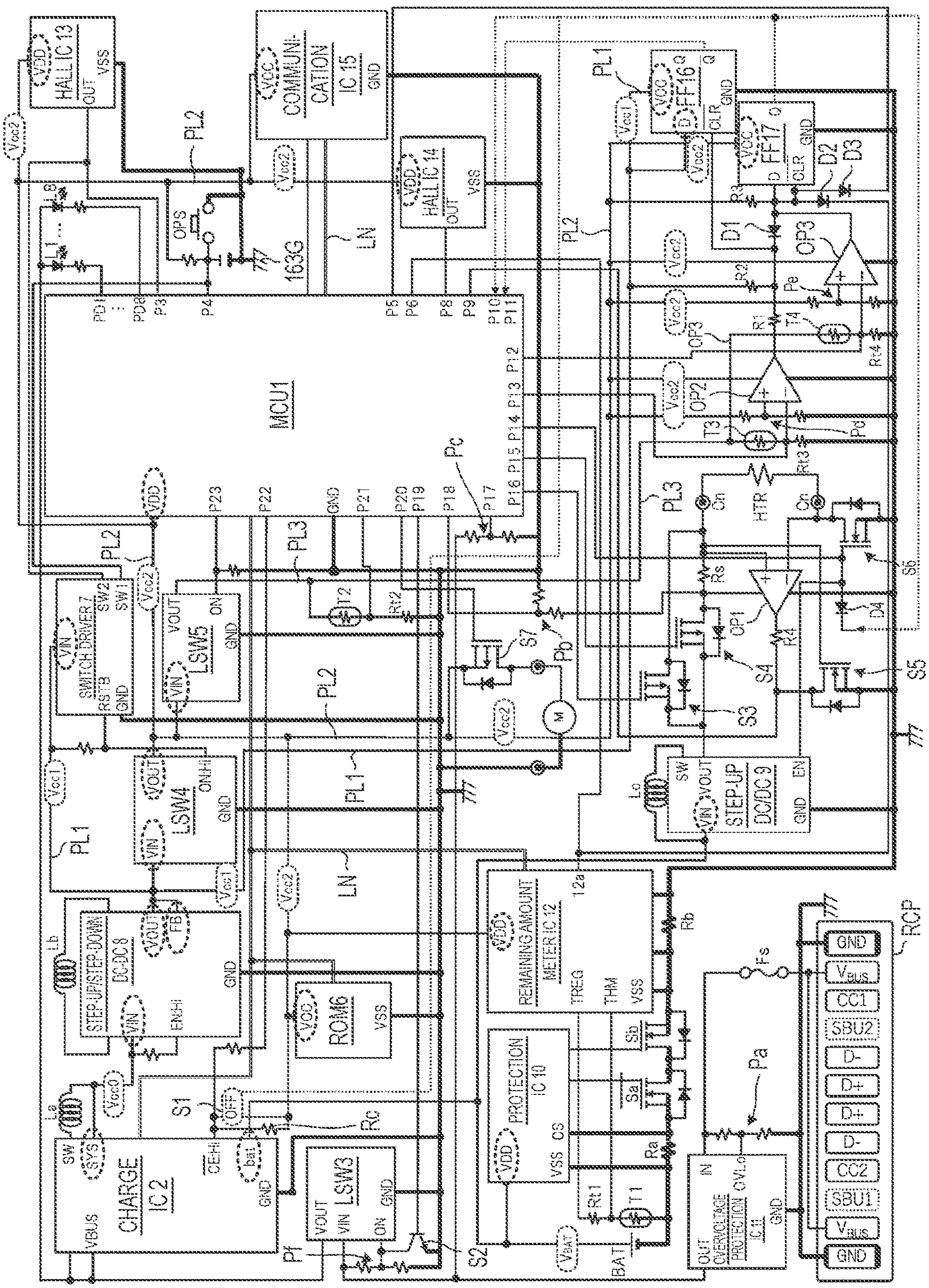
FIG. 14 is a diagram for illustrating an operation of the electric circuit in a sleep mode.
Figure 15:
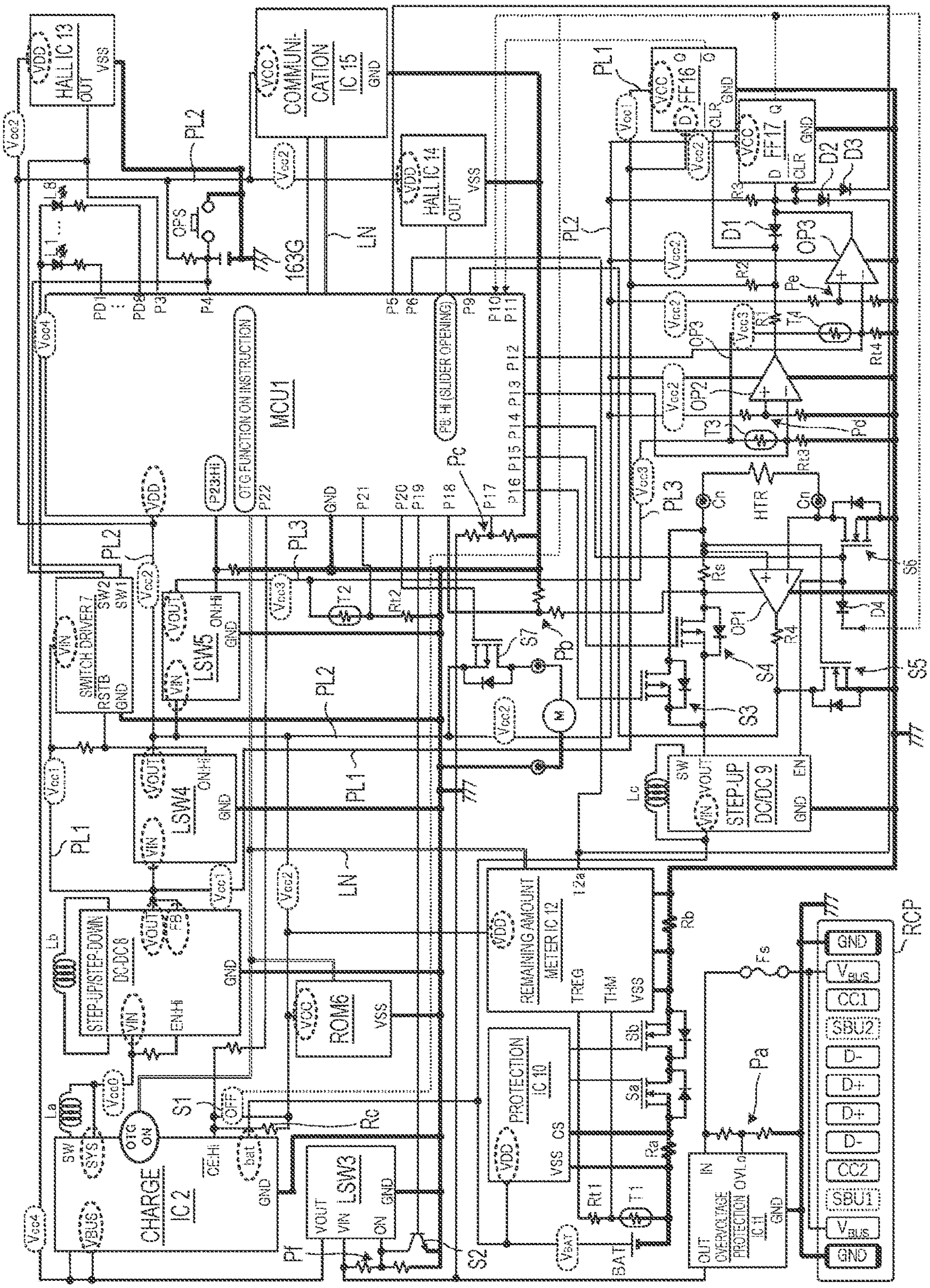
FIG. 15 is a diagram for illustrating an operation of the electric circuit in an active mode.
Figure 16:
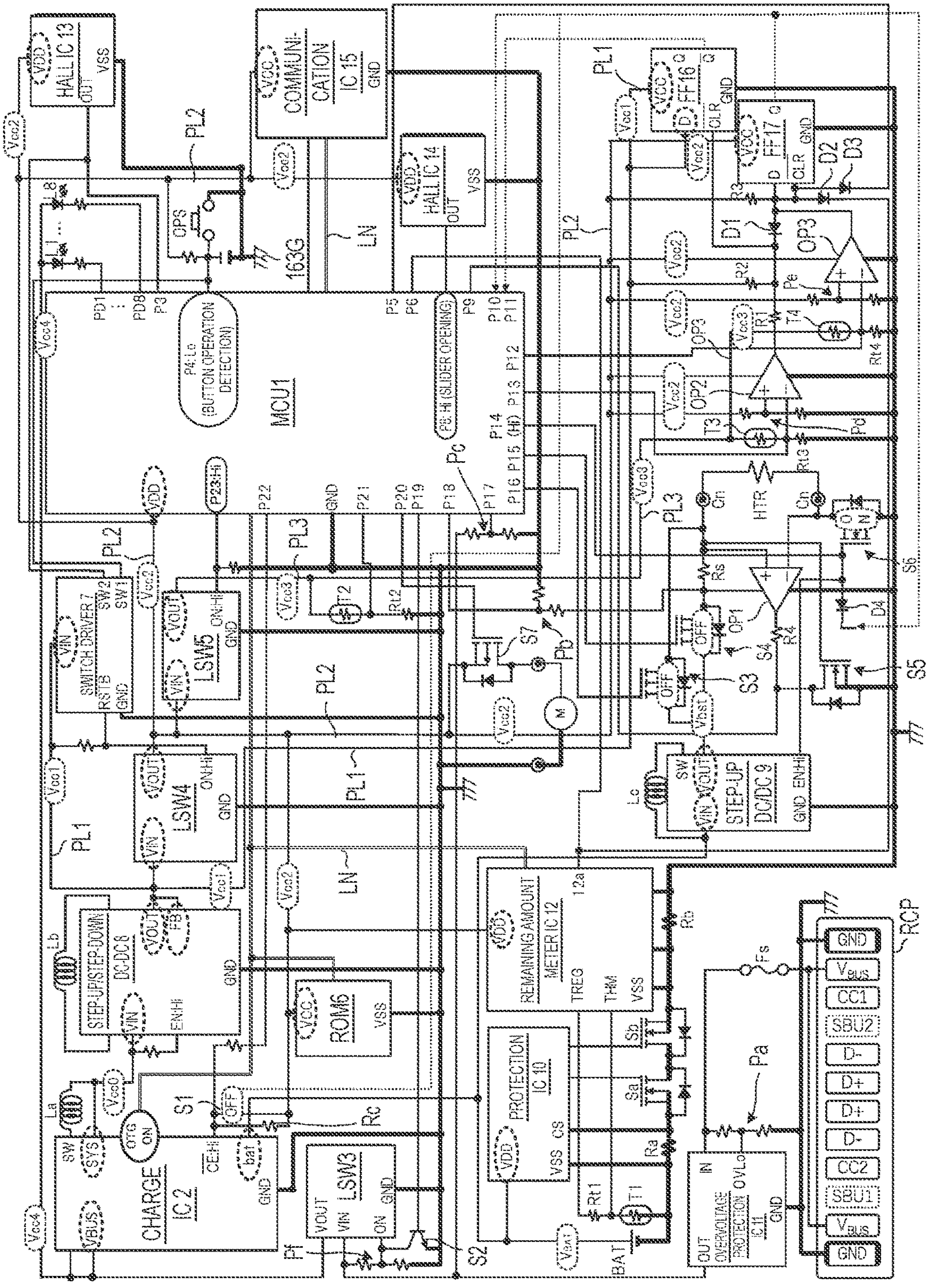
FIG. 16 is a diagram for illustrating an operation of the electric circuit in a heating initial setting mode.
Figure 17:
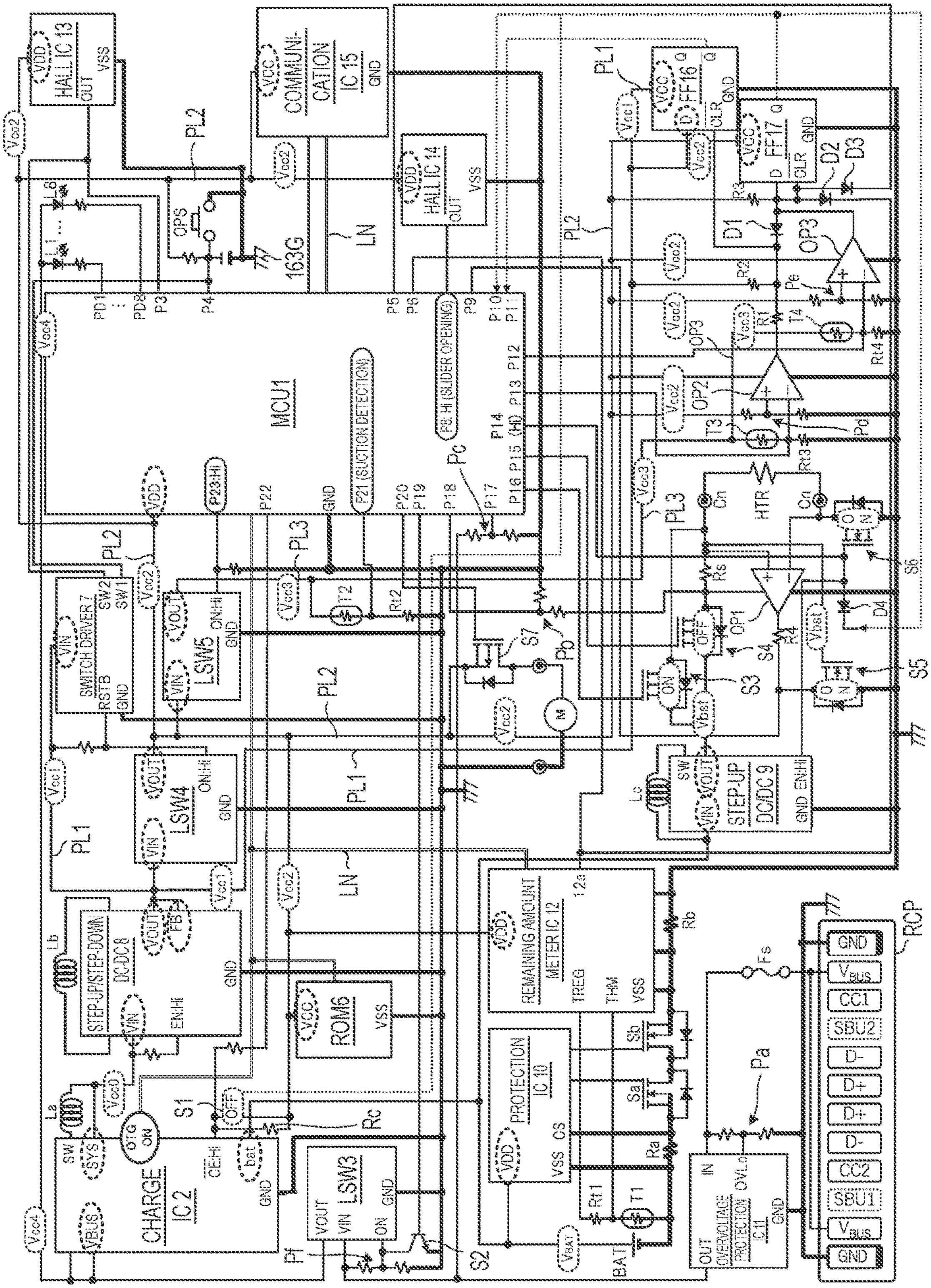
FIG. 17 is a diagram for illustrating an operation of the electric circuit when a heater is heated in a heating mode.
Figure 18:
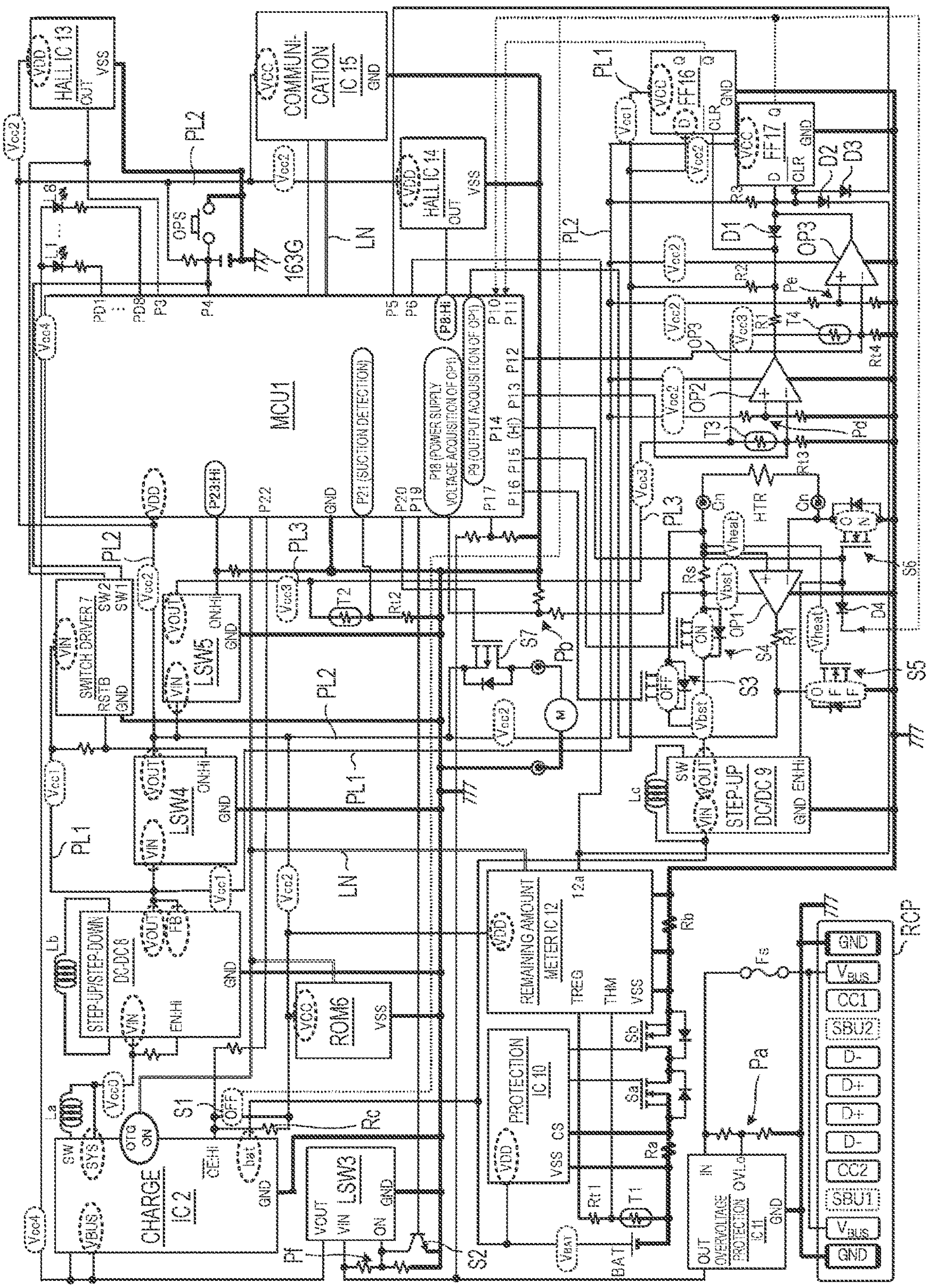
FIG. 18 is a diagram for illustrating an operation of the electric circuit when a temperature of the heater is detected in the heating mode.
Figure 19:
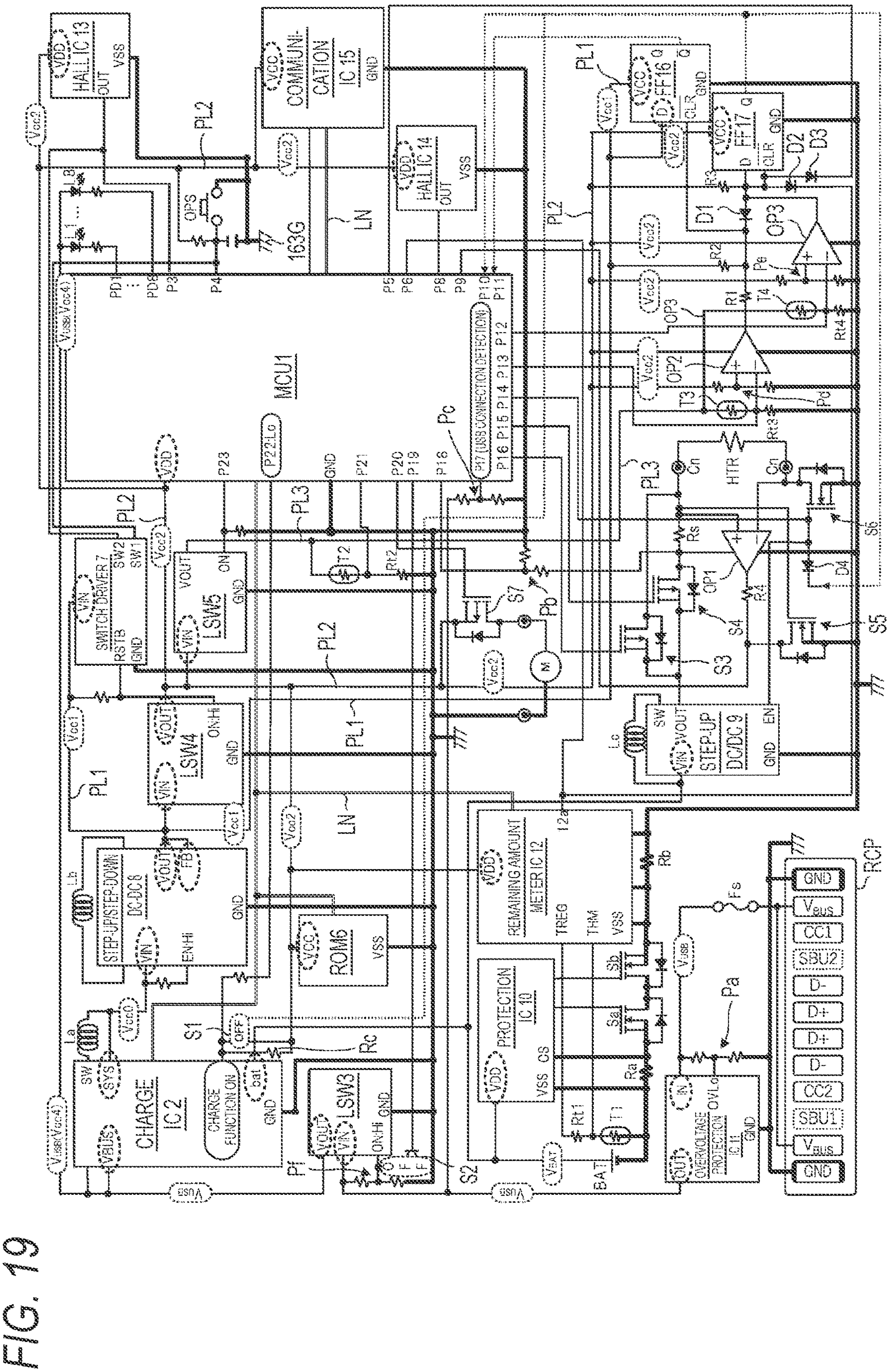
FIG. 19 is a diagram for illustrating an operation of the electric circuit in a charge mode.
Figure 20:
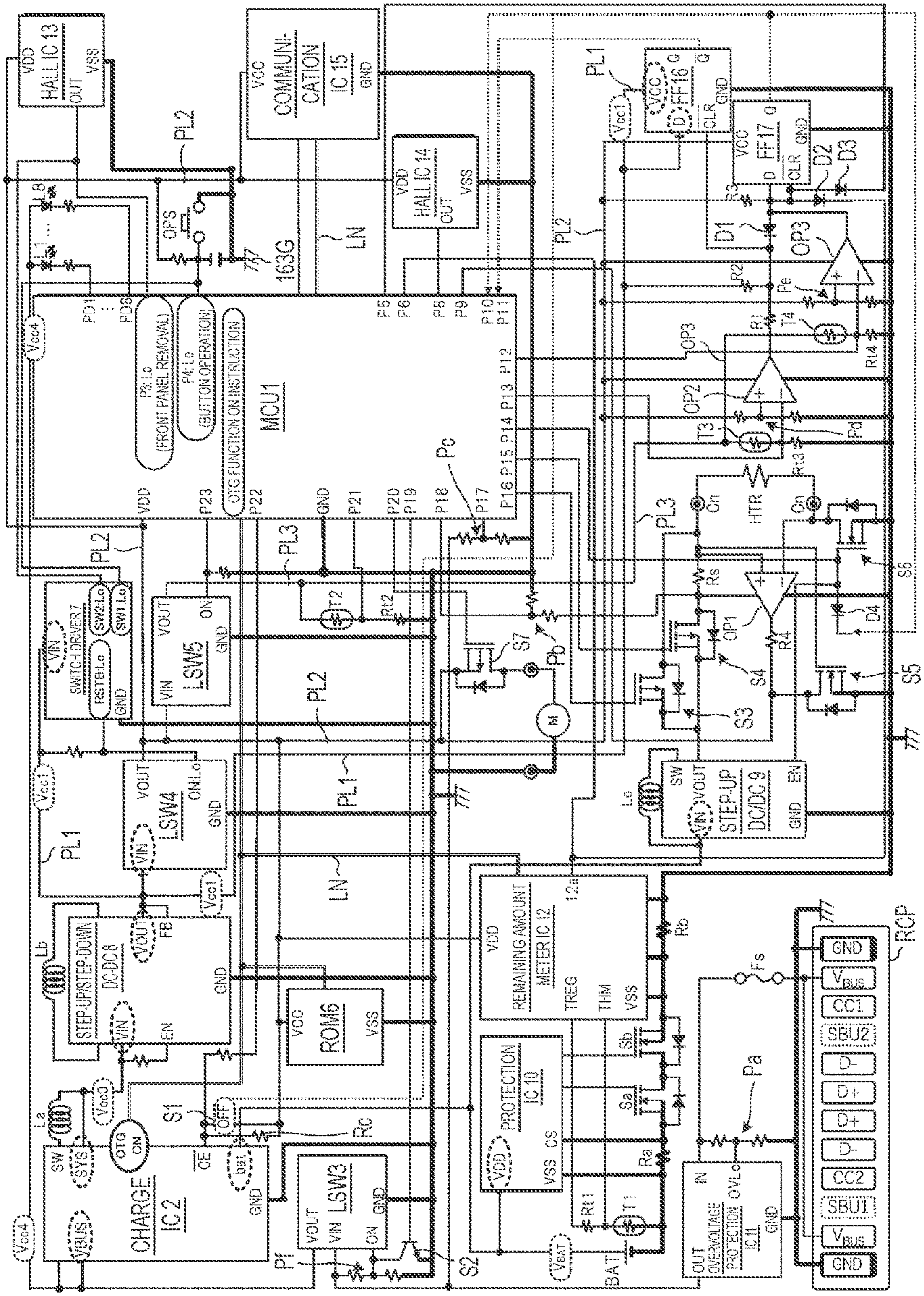
FIG. 20 is a diagram for illustrating an operation of the electric circuit when an MCU is reset (restarted)

FIG. 14 is a diagram for illustrating an operation of the electric circuit in the sleep mode. FIG. 15 is a diagram for illustrating an operation of the electric circuit in the active mode. FIG. 16 is a diagram for illustrating an operation of the electric circuit in the heating initial setting mode. FIG. 17 is a diagram for illustrating an operation of the electric circuit when the heater HTR is heated in the heating mode. FIG. 18 is a diagram for illustrating an operation of the electric circuit when a temperature of the heater HTR is detected in the heating mode. FIG. 19 is a diagram for illustrating an operation of the electric circuit in the charge mode. FIG. 20 is a diagram for illustrating an operation of the electric circuit when the MCU 1 is reset (restarted). In each of FIGS. 14 to 20, among terminals of the electronic component formed into a chip, a terminal surrounded by a dashed ellipse indicates a terminal to which the power supply voltage $V_{BAT}$, the USB voltage $V_{USB}$, the system power supply voltage, or the like is input or output.

In any operation mode, the power supply voltage $V_{BAT}$ is input to the power supply terminal VDD of the protection IC 10, the input terminal VIN of the step-up DC/DC converter 9, and the charge terminal bat of the charge IC 2.

<Sleep Mode: FIG. 14>

The MCU 1 enables the $V_{BAT}$ power path function of the charge IC 2, and disables the OTG function and the charge function of the charge IC 2. Since the USB voltage $V_{USB}$ is not input to the input terminal VBUS of the charge IC 2, the $V_{BAT}$ power path function of the charge IC 2 is enabled. Since a signal for enabling the OTG function is not output from the MCU 1 to the charge IC 2 through the communication line LN, the OTG function is disabled. Therefore, the charge IC 2 generates the system power supply voltage Vcc0 from the power supply voltage $V_{BAT}$ input to the charge terminal bat, and outputs the generated system power supply voltage Vcc0 from the output terminal SYS. The system power supply voltage Vcc0 output from the output terminal SYS is input to the input terminal VIN and the enable terminal EN of the step-up/step-down DC/DC converter 8. The step-up/step-down DC/DC converter 8 is enabled when the high-level system power supply voltage Vcc0 is input to the enable terminal EN having the positive logic, generates the system power supply voltage Vcc1 from the system power supply voltage Vcc0, and outputs the generated system power supply voltage Vcc1 from the output terminal VOUT. The system power supply voltage Vcc1 output from the output terminal VOUT of the step-up/step-down DC/DC converter 8 is supplied to the input terminal VIN of the LSW 4, the control terminal ON of the LSW 4, the input terminal VIN of the switch driver 7, and the power supply terminal VCC and the D terminal of the FF 16.

When the system power supply voltage Vcc1 is input to the control terminal ON, the LSW 4 outputs the system power supply voltage Vcc1 input to the input terminal VIN as the system power supply voltage Vcc2 from the output terminal VOUT. The system power supply voltage Vcc2 output from the LSW 4 is input to the power supply terminal VDD of the MCU 1, the input terminal VIN of the LSW 5, the power supply terminal VDD of the Hall IC 13, the power supply terminal VCC of the communication IC 15, and the power supply terminal VDD of the Hall IC 14. Further, the system power supply voltage Vcc2 is supplied to the power supply terminal VDD of the remaining amount meter IC 12, the power supply terminal VCC of the ROM 6, the resistor Rc and the bipolar transistor S1 connected to the charge enable terminal CE ($\overline{\quad}$) of the charge IC 2, the power supply terminal VCC of the FF 17, the positive power supply terminal of the operational amplifier OP3, the voltage dividing circuit Pe, the positive power supply terminal of the operational amplifier OP2, and the voltage dividing circuit Pd. The bipolar transistor S1 connected to the charge IC 2 is turned off unless a low-level signal is output from the Q terminal of the FF 17. Therefore, the system power supply voltage Vcc2 generated by the LSW 4 is also input to the charge enable terminal CE ($\overline{\quad}$) of the charge IC 2. Since the charge enable terminal CE ($\overline{\quad}$) of the charge IC 2 has the negative logic, the charge function of the charge IC 2 is turned off in the state.

In this way, in the sleep mode, since the LSW 5 stops outputting the system power supply voltage Vcc3, power supply to an electronic component connected to the power supply line PL3 is stopped. Further, in the sleep mode, since the OTG function of the charge IC 2 is stopped, power supply to the LEDs L1 to L8 is stopped.

<Active Mode: FIG. 15>

When detecting that a signal input to the terminal P8 is at a high level and the slider 119 is opened from the sleep mode state of FIG. 14, the MCU 1 inputs the high-level signal from the terminal P23 to the control terminal ON of the LSW 5. Accordingly, the LSW 5 outputs the system power supply voltage Vcc2 input to the input terminal VIN from the output terminal VOUT as the system power supply voltage Vcc3. The system power supply voltage Vcc3 output from the output terminal VOUT of the LSW 5 is supplied to the thermistor T2, the thermistor T3, and the thermistor T4.

Further, when detecting that the slider 119 is opened, the MCU 1 enables the OTG function of the charge IC 2 via the communication line LN. Accordingly, the charge IC 2 outputs, from the input terminal VBUS, the system power supply voltage Vcc4 obtained by stepping up the power supply voltage $V_{BAT}$ input from the charge terminal bat. The system power supply voltage Vcc4 output from the input terminal VBUS is supplied to the LEDs L1 to L8.

<Heating Initial Setting Mode: FIG. 16>

When a signal input to the terminal P4 is at a low level (the operation switch OPS is pressed) from the state of FIG. 15, the MCU 1 performs various settings necessary for heating, and then inputs a high level enable signal from the terminal P14 to the enable terminal EN of the step-up DC/DC converter 9. Accordingly, the step-up DC/DC converter 9 outputs a drive voltage $V_{bst}$ obtained by stepping up the power supply voltage $V_{BAT}$ from the output terminal VOUT. The drive voltage $V_{bst}$ is supplied to the switch S3 and the switch S4. In the state, the switch S3 and the switch S4 are turned off. Further, the switch S6 is turned on by the high-level enable signal output from the terminal P14. Accordingly, a negative electrode side terminal of the heater HTR is connected to the ground line, and when the switch S3 is turned on, the heater HTR is in a heatable state. After the high-level enable signal is output from the terminal P14 of the MCU 1, the processing is shifted to the heating mode.

<Heating of Heater in Heating Mode: FIG. 17>

In the state of FIG. 16, the MCU 1 starts switching control of the switch S3 connected to the terminal P16 and switching control of the switch S4 connected to the terminal P15. These switching controls may be automatically started when the heating initial setting mode described above is completed, or may be started by further pressing the operation switch OPS. Specifically, as shown in FIG. 17, the MCU 1 performs heating control of turning on the switch S3, turning off the switch S4, supplying the drive voltage $V_{bst}$ to the heater HTR, and heating the heater HTR for aerosol generation, and as shown in FIG. 18, the MCU 1 performs temperature detection control of turning off the switch S3, turning on the switch S4, and detecting a temperature of the heater HTR.

As shown in FIG. 17, during the heating control, the drive voltage $V_{bst}$ is also supplied to a gate of the switch S5, and the switch S5 is turned on. Further, during the heating control, the drive voltage $V_{bst}$ that passes through the switch S3 is also input to the positive power supply terminal of the operational amplifier OP1 via the resistor Rs. A resistance value of the resistor Rs is negligibly smaller than an internal resistance value of the operational amplifier OP1. Therefore, during the heating control, a voltage input to the positive power supply terminal of the operational amplifier OP1 is substantially equal to the drive voltage $V_{bst}$.

A resistance value of the resistor R4 is larger than an on-resistance value of the switch S5. The operational amplifier OP1 operates also during the heating control, but the switch S5 is turned on during the heating control. In a state where the switch S5 is turned on, an output voltage of the operational amplifier OP1 is divided by a voltage dividing circuit of the resistor R4 and the switch S5, and is input to the terminal P9 of the MCU 1. Since the resistance value of the resistor R4 is larger than the on-resistance value of the switch S5, a voltage input to the terminal P9 of the MCU 1 is sufficiently small. Accordingly, a large voltage can be prevented from being input from the operational amplifier OP1 to the MCU 1.

<Heater Temperature Detection in Heating Mode: FIG. 18>

As shown in FIG. 18, during the temperature detection control, the drive voltage $V_{bst}$ is input to the positive power supply terminal of the operational amplifier OP1 and is also input to the voltage dividing circuit Pb. A voltage divided by the voltage dividing circuit Pb is input to the terminal P18 of the MCU 1. The MCU 1 acquires a reference voltage $V_{temp}$ applied to a series circuit of the resistor Rs and the heater HTR during the temperature detection control based on a voltage input to the terminal P18.

During the temperature detection control, the drive voltage $V_{bst}$ (reference voltage $V_{temp}$) is supplied to the series circuit of the resistor Rs and the heater HTR. Then, a voltage $V_{heat}$ obtained by dividing the drive voltage $V_{bst}$ (reference voltage $V_{temp}$) by the resistor Rs and the heater HTR is input to the non-inverting input terminal of the operational amplifier OP1. Since the resistance value of the resistor Rs is sufficiently larger than the resistance value of the heater HTR, the voltage $V_{heat}$ is a value sufficiently lower than the drive voltage $V_{bst}$. During the temperature detection control, the low voltage $V_{heat}$ is also supplied to the gate terminal of the switch S5, so that the switch S5 is turned off. The operational amplifier OP1 amplifies and outputs a difference between a voltage input to the inverting input terminal and the voltage $V_{heat}$ input to the non-inverting input terminal.

An output signal of the operational amplifier OP1 is input to the terminal P9 of the MCU 1. The MCU 1 acquires a temperature of the heater HTR based on a signal input to the terminal P9, the reference voltage $V_{temp}$ acquired based on the input voltage of the terminal P18, and a known electrical resistance value of the resistor Rs. The MCU 1 performs heating control of the heater HTR based on the acquired temperature of the heater HTR. The heating control of the heater HTR includes control of discharge from the power supply BAT to the heater HTR, control such that the temperature of the heater HTR becomes a target temperature, and the like.

The MCU 1 can acquire a temperature of the heater HTR even in a period during which the switch S3 and the switch S4 are turned off (a period during which the heater HTR is not energized). Specifically, the MCU 1 acquires the temperature of the heater HTR based on a voltage input to the terminal P13 (an output voltage of a voltage dividing circuit including the thermistor T3 and the resistor Rt3).

The MCU 1 can also acquire a temperature of the case 110 at an optional timing. Specifically, the MCU 1 acquires the temperature of the case 110 based on a voltage input to the terminal P12 (an output voltage of a voltage dividing circuit including the thermistor T4 and the resistor Rt4).

<Charge Mode: FIG. 19>

FIG. 19 illustrates a case where the USB connection is performed in a state of the sleep mode. When the USB connection is performed, the USB voltage $V_{USB}$ is input to the input terminal VIN of the LSW 3 via the overvoltage protection IC 11. The USB voltage $V_{USB}$ is also supplied to the voltage dividing circuit Pf connected to the input terminal VIN of the LSW 3. Since the bipolar transistor S2 is turned on at a time point immediately after the USB connection is performed, a signal input to the control terminal ON of the LSW 3 remains at a low level. The USB voltage $V_{USB}$ is also supplied to the voltage dividing circuit Pc connected to the terminal P17 of the MCU 1, and a voltage divided by the voltage dividing circuit Pc is input to the terminal P17. The MCU 1 detects that the USB connection is performed based on the voltage input to the terminal P17.

When detecting that the USB connection is performed, the MCU 1 turns off the bipolar transistor S2 connected to the terminal P19. When a low-level signal is input to a gate terminal of the bipolar transistor S2, the USB voltage $V_{USB}$ divided by the voltage dividing circuit Pf is input to the control terminal ON of the LSW 3. Accordingly, a high-level signal is input to the control terminal ON of the LSW 3, the LSW 3 outputs the USB voltage $V_{USB}$ from the output terminal VOUT. The USB voltage $V_{USB}$ output from the LSW 3 is input to the input terminal VBUS of the charge IC 2. Further, the USB voltage $V_{USB}$ output from the LSW 3 is supplied to the LEDs L1 to L8 as the system power supply voltage Vcc4 as it is without passing through the charge IC 2.

When detecting that the USB connection is performed, the MCU 1 further outputs a low-level enable signal from the terminal P22 to the charge enable terminal CE ($\overline{\ }$) of the charge IC 2. Accordingly, the charge IC 2 enables the charge function of the power supply BAT, and starts charging the power supply BAT by the USB voltage $V_{USB}$ input to the input terminal VBUS. At this time, the MCU 1 does not perform heating of the heater HTR for generating the aerosol while the switch S3 and the switch S4 are turned off. In other words, when detecting that the USB connection is performed based on a voltage input to the terminal P17, the MCU 1 prohibits a power supply from the power supply BAT to the heater connector Cn. Therefore, the receptacle RCP and the overvoltage protection IC 11, which are electronic components that function only during charge, are electronic components that function when voltage conversion control associated with the heating control is not executed.

In a case where the USB connection is performed in a state of the active mode, when detecting that the USB connection is performed, the MCU 1 turns off the bipolar transistor S2 connected to the terminal P19, outputs a low-level enable signal from the terminal P22 to the charge enable terminal CE ($\overline{\ }$) of the charge IC 2, and turns off the OTG function of the charge IC 2 by the serial communication that uses the communication line LN. Accordingly, the system power supply voltage Vcc4 supplied to the LEDs L1 to L8 is switched from a voltage (a voltage based on the power supply voltage $V_{BAT}$) generated by the OTG function of the charge IC 2 to the USB voltage $V_{USB}$ output from the LSW 3. The LEDs L1 to L8 do not operate unless the built-in switch is controlled to be turned on by the MCU 1. Therefore, an unstable voltage in a transition period from turning on to turning off the OTG function is prevented from being supplied to the LEDs L1 to L8.

<Reset of MCU: FIG. 20>

When the outer panel 115 is removed, an output of the Hall IC 13 is at a low level, the operation switch OPS is operated to be turned on, and a signal input to the terminal P4 of the MCU 1 is at a low level, both the terminal SW1 and the terminal SW2 of the switch driver 7 are at a low level. Accordingly, the switch driver 7 outputs a low-level signal from the reset input terminal RSTB. A low-level signal output from the reset input terminal RSTB is input to the control terminal ON of the LSW 4. Accordingly, the LSW 4 stops outputting the system power supply voltage Vcc2 from the output terminal VOUT. When the output of the system power supply voltage Vcc2 is stopped, since the system power supply voltage Vcc2 is not input to the power supply terminal VDD of the MCU 1, the MCU 1 is stopped.

When a time during which the low-level signal is output from the reset input terminal RSTB reaches a predetermined time or when a signal input to any one of the terminal SW1 and the terminal SW2 is at a high level, the switch driver 7 returns the signal output from the reset input terminal RSTB to a high level. Accordingly, the control terminal ON of the LSW 4 is at a high level, and a state where the system power supply voltage Vcc2 is supplied to each unit is restored.

<Detailed Description of Board>

Next, an arrangement of the ICs and the elements mounted on the MCU-mounted board 161 and the receptacle-mounted board 162 will be described.

[Receptacle-Mounted Board]

Figure 21:
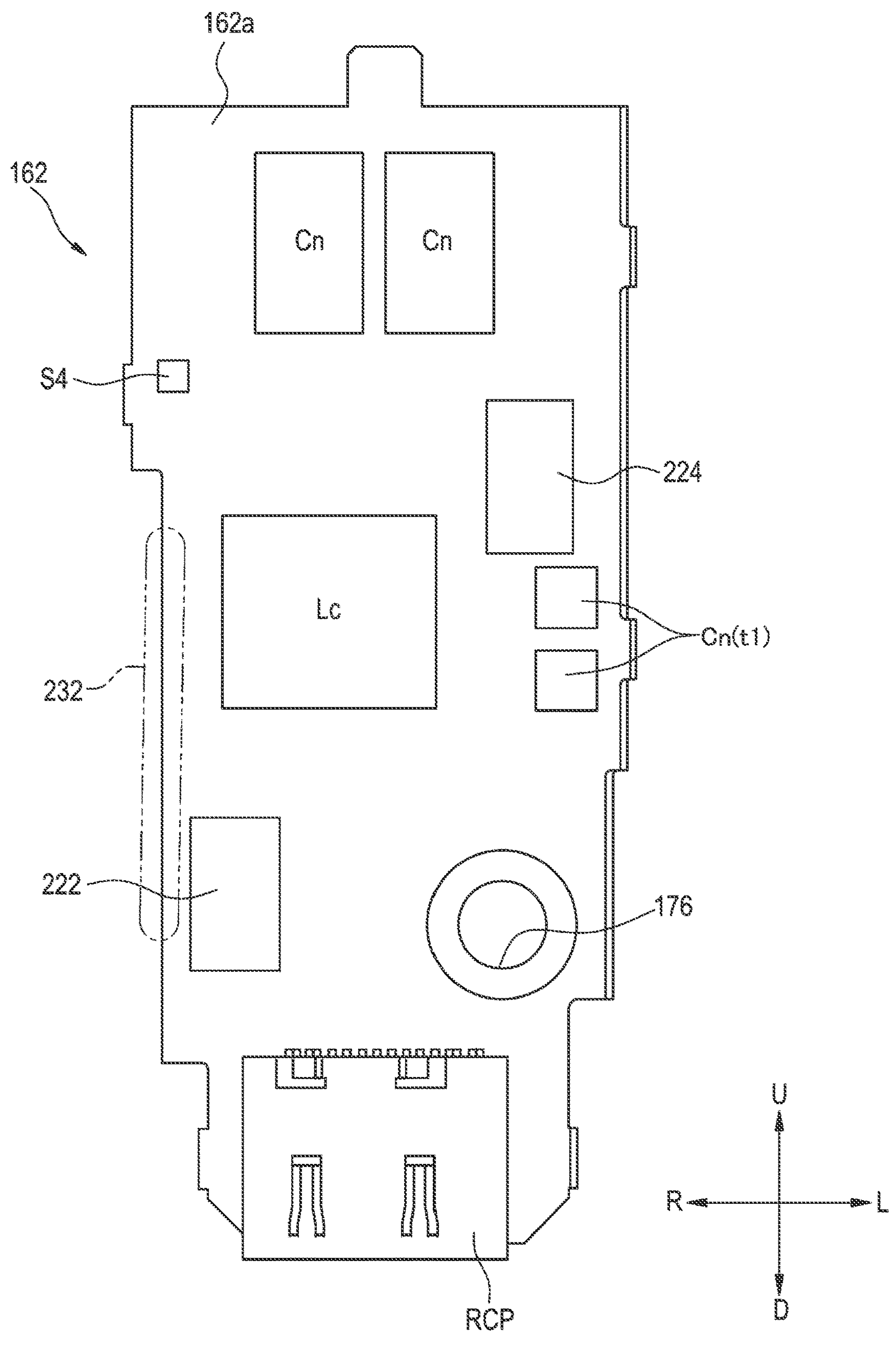
FIG. 21 is a diagram showing a main surface of a receptacle-mounted board.

FIG. 21 is a diagram showing the main surface 162*a* of the receptacle-mounted board 162. On the main surface 162*a* of the receptacle-mounted board 162 that extends in the upper-lower direction, the heater connectors Cn are mounted on an upper end portion, the receptacle RCP is mounted on a lower end portion, and the reactor Lc of the step-up DC/DC converter 9 is mounted between the heater connectors Cn and the receptacle RCP.

In the vicinity of the receptacle RCP, a battery connector 222 on a positive electrode side (hereinafter, referred to as positive-electrode-side battery connector 222) is mounted on an upper right side, and an opening portion 176 that fixes a spacer 173 is disposed on an upper left side. Further, a battery connector 224 on a negative electrode side (hereinafter, referred to as negative-electrode-side battery connector 224) and power supply temperature detection connectors Cn (t1) connected to the thermistor T1 that constitutes the power supply temperature sensor are mounted on a left side of the reactor Lc, and the switch S4 for detecting a temperature of the heater HTR is mounted on a side opposite to the negative-electrode-side battery connector 224 in the left-right direction. The positive-electrode-side power supply bus bar 236 (see FIGS. 7 and 8) that extends from the positive electrode terminal of the power supply BAT is connected to the positive-electrode-side battery connector 222, and the negative-electrode-side power supply bus bar 238 (see FIGS. 7 and 8) that extends from the negative electrode terminal of the power supply BAT is connected to the negative-electrode-side battery connector 224.

The opening portion 176 of the receptacle-mounted board 162 that fixes the spacer 173 is provided at a position close to the receptacle RCP mounted on the lower end portion, in other words, on a lower end portion side of the upper end portion with respect to a center. In the vicinity of a path through which power supplied from the external power supply passes, noise due to the current may be generated, but by providing the spacer 173 not influenced by the noise in the vicinity of the path, a board area of the receptacle-mounted board 162 can be effectively utilized.

Further, the positive-electrode-side battery connector 222 that electrically connects the power supply BAT and the receptacle-mounted board 162 is provided at a position close to the receptacle RCP mounted on the lower end portion, in other words, below the center in the upper-lower direction. Although the positive-electrode-side battery connector 222, which is a conductor, is not a little influenced by the noise, since a large current passes through the positive-electrode-side battery connector 222, the influence of the noise is slight. Therefore, a board area of the receptacle RCP can be effectively utilized by providing the positive-electrode-side battery connector 222 in the vicinity of the path. With these contrivances, since a size of the receptacle-mounted board 162 can be prevented from being increased, a cost and a size of the inhaler 100 can be reduced.

Figure 22:
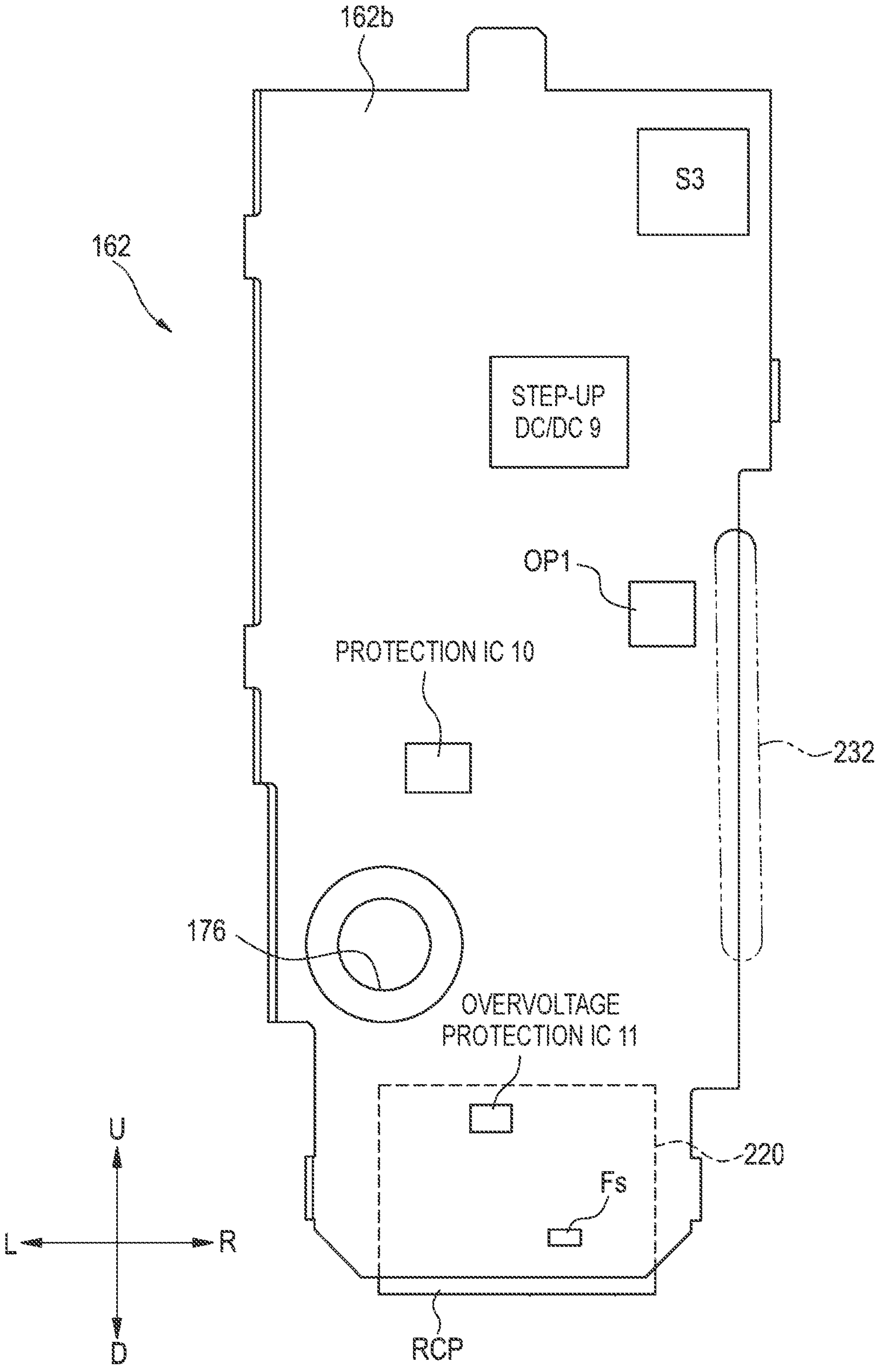
FIG. 22 is a diagram showing a secondary surface of the receptacle-mounted board.

FIG. 22 is a diagram showing the secondary surface 162*b* of the receptacle-mounted board 162. The step-up DC/DC converter 9, the operational amplifier OP1, the protection IC 10, the overvoltage protection IC 11, the fuse Fs, and the switch S3 for generating the aerosol are mounted on the secondary surface 162*b* of the receptacle-mounted board 162 that extends in the upper-lower direction.

The overvoltage protection IC 11 and the fuse Fs are mounted below the opening portion 176. In this way, since the overvoltage protection IC 11 and the fuse Fs are mounted on the secondary surface 162*b* on a side opposite to the main surface 162*a* on which the receptacle RCP is mounted, as compared with a case where the overvoltage protection IC 11 and the fuse Fs are mounted on the same surface as that of the receptacle RCP, a board area can be effectively utilized, and a size of the receptacle-mounted board 162 can be prevented from being increased. Accordingly, the cost and the size of the inhaler 100 can be reduced.

The overvoltage protection IC 11 is mounted at a position that overlaps the receptacle RCP when viewed from a direction (front-rear direction) perpendicular to an element arrangement surface of the receptacle-mounted board 162, that is, in a receptacle projection region 220 that is a portion where the receptacle RCP is projected in the front-rear direction. Therefore, a distance between a $V_{BUS}$ pin pair of the receptacle RCP and the overvoltage protection IC 11 can be minimized, and an influence of power before being protected by the overvoltage protection IC 11 on other electrical components mounted on the receptacle-mounted board 162 can be reduced. Accordingly, durability of the inhaler 100 can be improved, and an operation thereof can be stabilized.

The step-up DC/DC converter 9, the operational amplifier OP1, the protection IC 10, and the switch S3 for generating the aerosol are mounted above the opening portion 176.

The switch S3 for generating the aerosol is mounted on a right upper end portion of the secondary surface 162*b* of the receptacle-mounted board 162. The operational amplifier OP1 is mounted in the vicinity of a right end portion of a substantial center in the upper-lower direction of the secondary surface 162*b* of the receptacle-mounted board 162. The step-up DC/DC converter 9 is mounted between the switch S3 for generating the aerosol and the operational amplifier OP1 in the upper-lower direction and on a left side with respect to the switch S3 for generating the aerosol and the operational amplifier OP1 in the left-right direction. The protection IC 10 is mounted between the operational amplifier OP1 and the opening portion 176 in the upper-lower direction, and between the step-up DC/DC converter 9 and the opening portion 176 in the left-right direction.

[MCU-Mounted Board]

Figure 23:
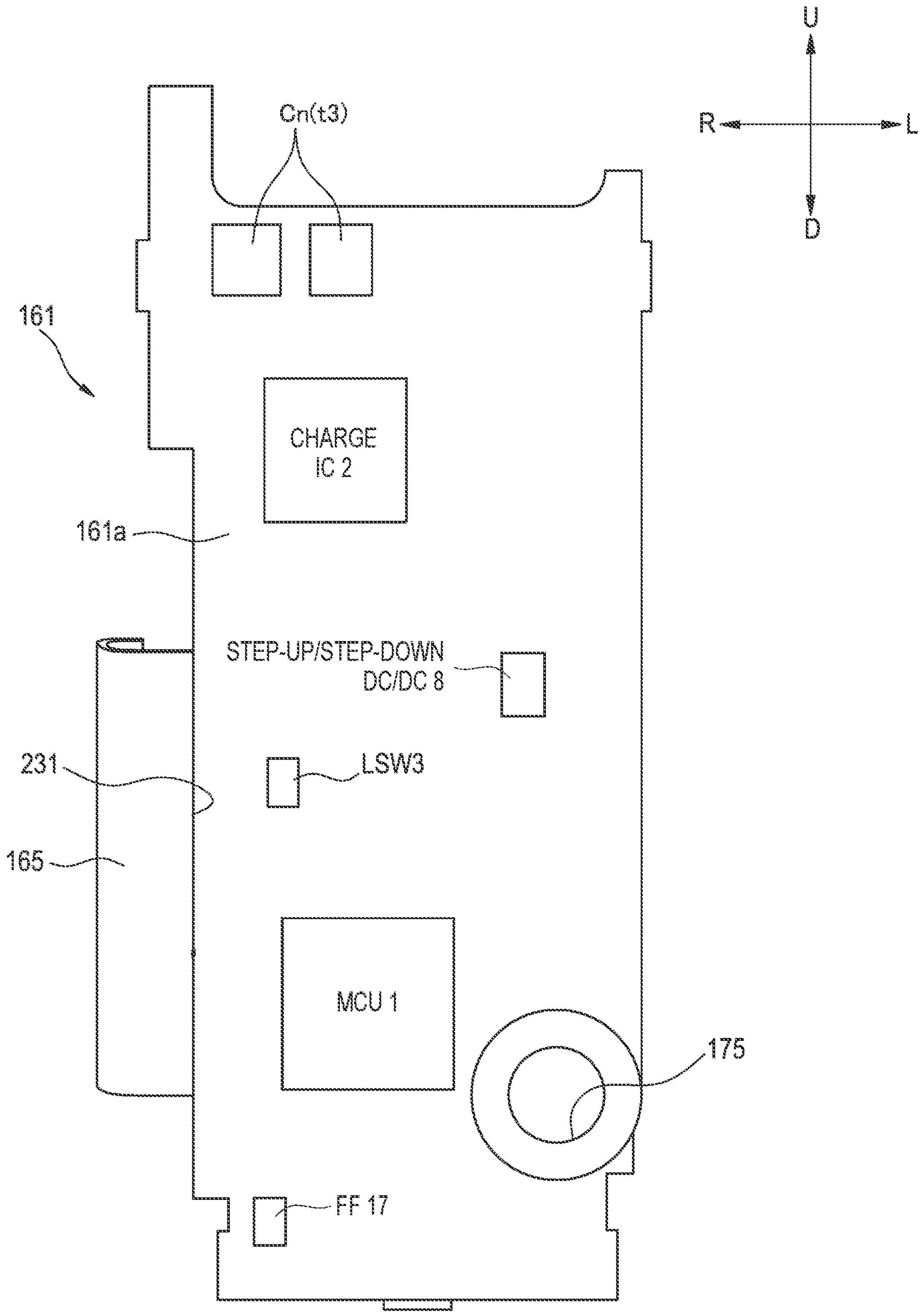
FIG. 23 is a diagram showing a main surface of an MCU-mounted board.

FIG. 23 is a diagram showing the main surface 161*a* of the MCU-mounted board 161. In the main surface 161*a* of the MCU-mounted board 161 that extends in the upper-lower direction, an opening portion 175 that fixes the spacer 173 is disposed at a position corresponding to the opening portion 176 of the receptacle-mounted board 162, and the MCU 1 is mounted in the vicinity of the opening portion 175.

Heater temperature detection connectors Cn (t3) to which the thermistor T3 that constitutes the heater temperature sensor is connected via a conductive wire, the charge IC 2, the LSW 3, the step-up/step-down DC/DC converter 8, and the FF 17 are mounted on the main surface 161*a* of the MCU-mounted board 161.

The heater temperature detection connector Cn (t3) is mounted on an upper end portion of the main surface 161*a* of the MCU-mounted board 161.

The charge IC 2 is mounted below the heater temperature detection connectors Cn (t3) and above a vertical center of the main surface 161*a*.

The LSW 3 is mounted between the charge IC 2 and the MCU 1.

The step-up/step-down DC/DC converter 8 is mounted on a left side of the LSW 3 and between the charge IC 2 and the LSW 3 in the upper-lower direction.

The FF 17 is mounted on a right lower end portion below the opening portion 175 and the MCU 1.

Figure 24:
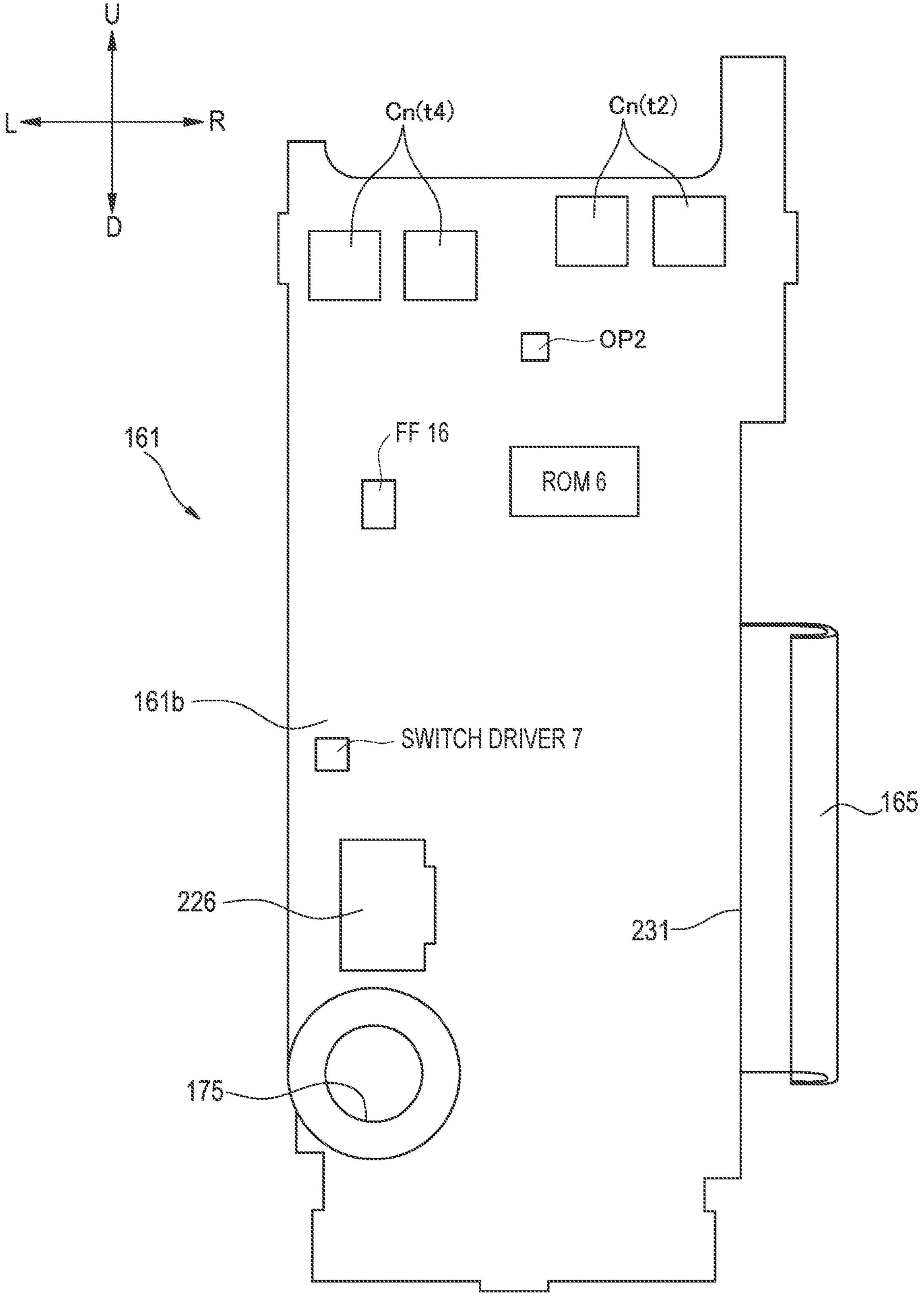
FIG. 24 is a diagram showing a secondary surface of the MCU-mounted board.

FIG. 24 is a diagram showing the secondary surface 161*b* of the MCU-mounted board 161. A motor connector 226 to which the vibration motor M is connected via a conductive wire, the switch driver 7, case temperature detection connectors Cn (t4) to which the thermistor T4 that constitutes the case temperature sensor is connected via a conductive wire, intake detection connectors Cn (t2) to which the thermistor T2 that constitutes the intake sensor is connected via a conductive wire, the FF 16, the ROM 6, and the operational amplifier OP2 are mounted on the secondary surface 161*b* of the MCU-mounted board 161 that extends in the upper-lower direction.

The motor connector 226 is mounted on an upper side of the opening portion 175. Further, the motor connector 226 is mounted on a left side with respect to a center in the left-right direction of the secondary surface 161*b* of the MCU-mounted board 161.

The switch driver 7 is mounted above the motor connector 226.

The case temperature detection connectors Cn (t4) and the intake detection connectors Cn (t2) are mounted on an upper end portion of the secondary surface 161*b* of the MCU-mounted board 161. In the present embodiment, the case temperature detection connectors Cn (t4) are mounted on a left end side in the left-right direction of the secondary surface 161*b* of the MCU-mounted board 161, and the intake detection connectors Cn (t2) are mounted on a right end side in the left-right direction of the secondary surface 161*b* of the MCU-mounted board 161.

The FF 16 is mounted between the case temperature detection connectors Cn (t4) and the switch driver 7. The FF 16 is mounted on a left end side in the left-right direction of the secondary surface 161*b* of the MCU-mounted board 161.

The ROM 6 is mounted on a right side of the FF 16. The ROM 6 is mounted slightly on a right side with respect to a lateral center of the secondary surface 161*b* of the MCU-mounted board 161.

The operational amplifier OP2 is mounted between the intake detection connectors Cn (t2) and the ROM 6. In the left-right direction of the secondary surface 161*b* of the MCU-mounted board 161, the operational amplifier OP2 is mounted between the intake detection connectors Cn (t2) and the case temperature detection connectors Cn (t4), and is mounted on a substantially lateral center of the secondary surface 161*b* of the MCU-mounted board 161.

The flexible wire board 165 that electrically connects the MCU-mounted board 161 and the receptacle-mounted board 162 connects FPC connection portions 231 and 232 of the MCU-mounted board 161 and the receptacle-mounted board 162 to each other. The FPC connection portion 231 is located at a right end portion of the MCU-mounted board 161 and at a position that extends downward from a substantially central portion in the upper-lower direction to a vicinity of the opening portion 175. The FPC connection portion 232 is located at a right end portion of the receptacle-mounted board 162 and at a position that extends downward from a substantially central portion in the upper-lower direction to a vicinity of the opening portion 176. Therefore, the flexible wire board 165 is mounted on the right end portion of the MCU-mounted board 161 and the right end portion of the receptacle-mounted board 162.

In this way, the operation switch OPS is not mounted on the MCU-mounted board 161 but is mounted on the LED-mounted board 163, and the receptacle RCP is not mounted on the MCU-mounted board 161 but is mounted on the receptacle-mounted board 162. In contrast, the MCU 1 is mounted on the MCU-mounted board 161.

Since the operation switch OPS is pressed by the user, the operation switch OPS is likely to serve as an entrance for the external noise such as static electricity to the internal unit 140. Since the USB Type-C shaped plug connected to an external power supply is inserted into and removed from the receptacle RCP by the user, the receptacle RCP is likely to serve as an entrance for the external noise such as the static electricity to the internal unit 140. The operation switch OPS and the receptacle RCP are not mounted on the MCU-mounted board 161 on which the MCU 1 is mounted, but are mounted on the circuit board different from the MCU-mounted board 161. Therefore, the MCU 1 can be disposed at a position away from the operation switch OPS and/or the receptacle RCP that is likely to serve as the entrance for the external noise to the internal unit 140. Accordingly, the MCU 1 can be prevented from malfunctioning or failing due to the external noise, and the durability of the inhaler 100 is improved.

Further, since the operation switch OPS and the receptacle RCP are mounted on different circuit boards, the operation switch OPS and the receptacle RCP, which are likely to serve as entrances for external noise to the internal unit 140, can be arranged apart from each other. Accordingly, even when external noises enter the internal unit 140 simultaneously from both the operation switch OPS and the receptacle RCP, since it is possible to prevent superimposition of both external noises, it is difficult to generate noise that is more difficult to cope with, and the durability of the inhaler 100 is improved.

The MCU 1 is mounted on a surface farther from the operation switch OPS and the receptacle RCP between the main surface 161*a* and the secondary surface 161*b* of the MCU-mounted board 161, that is, the main surface 161*a* in the present embodiment. In other words, the MCU 1 is mounted on a surface farther from the receptacle-mounted board 162 and the LED-mounted board 163 between the main surface 161*a* and the secondary surface 161*b* of the MCU-mounted board 161.

Accordingly, the MCU 1 can be disposed at a position as far as possible from the operation switch OPS and the receptacle RCP that are likely to serve as the entrances for the external noise to the internal unit 140. Therefore, the MCU 1 can be further prevented from malfunctioning or failing due to the external noise, and the durability of the inhaler 100 is further improved.

The ROM 6, the FF 16, and the FF 17 are mounted on the MCU-mounted board 161 on which the operation switch OPS and the receptacle RCP are not mounted.

Accordingly, the ROM 6, the FF 16, and the FF 17 can be away from the external noise that may enter the internal unit 140 via the operation switch OPS and/or the receptacle RCP. Therefore, the ROM 6, the FF 16, and the FF 17 can be prevented from malfunctioning or failing due to the external noise, and the durability of the inhaler 100 is improved.

The switch driver 7 is mounted on the MCU-mounted board 161 on which the operation switch OPS and the receptacle RCP are not mounted.

Accordingly, the switch driver 7 can be away from the external noise that may enter the internal unit 140 via the operation switch OPS and/or the receptacle RCP. Therefore, the switch driver 7 can be prevented from malfunctioning or failing due to the external noise, and the durability of the inhaler 100 is improved.

The overvoltage protection IC 11 and the fuse Fs are not mounted on the MCU-mounted board 161 on which the MCU 1 is mounted, but are mounted on the receptacle-mounted board 162 on which the receptacle RCP is mounted.

Therefore, even when the external noise enters the internal unit 140 via the receptacle RCP, since the overvoltage protection IC 11 and the fuse Fs are mounted on the receptacle-mounted board 162, the external noise that enters the internal unit 140 via the receptacle RCP can be prevented from entering a circuit board other than the receptacle-mounted board 162. Accordingly, an electronic component mounted on the circuit board other than the receptacle-mounted board 162 can be prevented from malfunctioning or failing due to the external noise, and the durability of the inhaler 100 is improved.

The number of electronic components mounted on the MCU-mounted board 161 on which the operation switch OPS is not mounted is larger than the number of electronic components mounted on the LED-mounted board 163 on which the operation switch OPS is mounted.

Therefore, since it is possible to reduce the number of electronic components mounted on the LED-mounted board 163 into which the external noise may enter from the operation switch OPS, the durability of the inhaler 100 is improved.

Although an embodiment of the present disclosure has been described above with reference to the accompanying drawings, it is needless to say that the present disclosure is not limited to the embodiment. It will be apparent to those skilled in the art that various changes and modifications may be conceived within the scope of the claims. It is also understood that various changes and modifications belong to the technical scope of the present disclosure. Further, constituent elements in the embodiment described above may be combined freely within a range not departing from the spirit of the present disclosure.

At least the following matters are described in the present description. Although corresponding constituent elements or the like in the above embodiment are shown in parentheses, the present disclosure is not limited thereto.

(1) Apower supply unit of an aerosol generation device (non-combustion-type inhaler 100), including:

a power supply (the power supply BAT);

a heater connector (the heater connector Cn) to which a heater (the heater HTR) configured to heat an aerosol source by consuming power supplied from the power supply is connected;

a controller (the MCU 1) configured to control a supply of power from the power supply to the heater;

a first circuit board (the MCU-mounted board 161);

a second circuit board (the receptacle-mounted board 162, the LED-mounted board 163) separated from the first circuit board; and a housing (the case 110) configured to accommodate the power supply, the heater connector, the controller, the first circuit board, and the second circuit board, in which an electronic component (the receptacle RCP, the operation switch OPS) disposed in a cavity provided in the housing is mounted only on the second circuit board among the first circuit board and the second circuit board, and in which the controller is mounted on the first circuit board.

The electronic component disposed in the cavity provided in the housing is likely to serve as an entrance for external noise such as static electricity.

According to (1), since such an electronic component is not mounted on the first circuit board on which the controller is mounted, but is mounted on the second circuit board, the controller can be disposed at a position away from the entrance for the external noise. Accordingly, the controller can be prevented from malfunctioning or failing due to the external noise, and durability of the power supply unit of the aerosol generation device is improved.

(2) The power supply unit of the aerosol generation device according to (1), further including:

a storage circuit (the ROM 6, the flip-flop 16) configured to store input information, in which the storage circuit is mounted on the first circuit board.

According to (2), since the storage circuit is mounted on the first circuit board, the storage circuit can be away from the external noise that may enter via the electronic component described above. Accordingly, the storage circuit can be prevented from malfunctioning or failing due to the external noise, and the durability of the power supply unit of the aerosol generation device is improved.

(3) The power supply unit of the aerosol generation device according to (1) or (2), further including:

a restart circuit (the switch driver 7) configured to restart the controller, in which the restart circuit is mounted on the first circuit board.

According to (3), since the restart circuit is mounted on the first circuit board, the restart circuit can be away from the external noise that may enter via the electronic component described above. Accordingly, the restart circuit can be prevented from malfunctioning or failing due to the external noise, and the durability of the power supply unit of the aerosol generation device is improved.

(4) The power supply unit of the aerosol generation device according to any one of (1) to (3), in which the first circuit board includes a first surface (the main surface 161*a*) and a second surface (the secondary surface 161*b*) that is a back surface of the first surface, and in which the controller is mounted on a surface farther from the second circuit board among the first surface and the second surface.

According to (4), the controller can be disposed at a position as far as possible from the entrance of the external noise. Therefore, the controller can be further prevented from malfunctioning or failing due to the external noise, and the durability of the power supply unit of the aerosol generation device is further improved.

(5) The power supply unit of the aerosol generation device according to any one of (1) to (4), further including:

a third circuit board (the LED-mounted board 163) separated from the first circuit board and the second circuit board;

a first electronic component (the receptacle RCP) disposed in the cavity provided in the housing; and a second electronic component (the operation switch OPS) disposed in the cavity provided in the housing, in which the first electronic component is mounted on the second circuit board, and in which the second electronic component is mounted on the third circuit board.

According to (5), since the first electronic component and the second electronic component are mounted on different circuit boards, the first electronic component and the second electronic component, both of which are arranged in the cavities provided in the housing and are likely to serve as entrances for the external noise such as static electricity, can be arranged apart from each other. Accordingly, even when external noises enter simultaneously from both the first electronic component and the second electronic component, since it is possible to prevent superimposition of the external noises, it is difficult to generate noise that is more difficult to cope with, and the durability of the power supply unit of the aerosol generation device is improved.

(6) The power supply unit of the aerosol generation device according to (1), further including:

a receptacle (the receptacle RCP) disposed in the cavity provided in the housing and electrically connected to an external power supply;

a charge IC (the charge IC 2) configured to control charge of the power supply by using power supplied from the receptacle; and a protection element (the overvoltage protection IC 11, the fuse Fs) configured to protect the charge IC from power supplied from the receptacle, in which the receptacle is mounted on the second circuit board, and in which the protection element is not mounted on the first circuit board, but is mounted on the second circuit board.

According to (6), even when the external noise enters via the receptacle, since the protection element is mounted on the second circuit board, the external noise that enters via the receptacle can be prevented from entering a circuit board other than the second circuit board. Accordingly, the electronic component mounted on the circuit board other than the second circuit board can be prevented from malfunctioning or failing due to the external noise, and the durability of the power supply unit of the aerosol generation device is improved.

(7) The power supply unit of the aerosol generation device according to (1), further including:

a physical switch (the operation switch OPS) disposed in the cavity provided in the housing and configured to be pressed by a user, in which the physical switch is mounted on the second circuit board, and is connected to ground (the ground 163G) when a user presses the physical switch.

When the physical switch is pressed by the user, the external noise such as static electricity is likely to enter.

According to (7), when pressed by the user, the physical switch is connected to the ground. Accordingly, when the physical switch is pressed by the user, even when the external noise enters from the physical switch, since the external noise can be released to the ground, the durability of the power supply unit of the aerosol generation device is improved.

(8) The power supply unit of the aerosol generation device according to (7), in which the ground is provided inside the second circuit board.

According to (8), since the ground is provided inside the second circuit board, when the physical switch is pressed by the user, even when the external noise enters from the physical switch, the external noise that enters from the physical switch can be prevented from entering a circuit board other than the second circuit board. Accordingly, an electronic component mounted on the circuit board other than the second circuit board can be prevented from malfunctioning or failing due to the external noise, and the durability of the power supply unit of the aerosol generation device is improved.

(9) The power supply unit of the aerosol generation device according to (8), in which the number of electronic components mounted on the first circuit board is larger than the number of electronic components mounted on the second circuit board.

According to (9), since it is possible to reduce the number of electronic components mounted on the second circuit board into which the external noise may enter from the first electronic component including the physical switch, the durability of the power supply unit of the aerosol generation device is improved.

The invention claimed is:

1. A power supply unit of an aerosol generation device which a heating unit is attachable to and detachable from, comprising:

a secondary battery;

a case forming a surface of the power supply unit;

a chassis accommodated in an internal space of the case and made of an insulating resin;

a plurality of magnets held by the chassis with a gap therebetween;

an inner member covering a side surface of the chassis; and an outer member covering an outer surface of the inner member, wherein the inner member includes a plurality of through holes exposing the plurality of magnets, and the outer member is replaceably fixed by the plurality of magnets exposed from the plurality of through holes.

2. The power supply unit according to claim 1, wherein the heating unit is configured by cooperation of an induction heating coil and a susceptor built in an attached rod.

3. The power supply unit according to claim 1, wherein the chassis includes a chassis main body holding the plurality of magnets, and a plate-shaped dividing wall perpendicular to the chassis main body and extending in a longer direction of the chassis main body, and the secondary battery is accommodated in a power supply accommodation space defined by the case and the dividing wall.

4. The power supply unit according to claim 3, further comprising:

a heating unit accommodation region defined in a side opposite to the power supply accommodation space with the dividing wall therebetween, wherein the heating unit is detachably accommodated in the heating unit accommodation region.

5. The power supply unit according to claim 3, further comprising:

an MCU;

an MCU-mounted board mounting the MCU; and a board accommodation region defined in a side opposite to the power supply accommodation space with the dividing wall therebetween, wherein the MCU-mounted board is accommodated in the board accommodation region.

6. The power supply unit according to claim 5, further comprising:

a receptacle configured to receive a power supply from an external power supply to charge the secondary battery; and a receptacle-mounted board which is separated from the MCU-mounted board and on which the receptacle is mounted.

7. The power supply unit according to claim 6, further comprising:

an operation switch operable by a user;

a plurality of LEDs; and an LED-mounted board which is separated from the MCU-mounted board and the receptacle-mounted board and on which the operation switch and the plurality of LEDs are mounted.

8. The power supply unit according to claim 7, wherein one end of the operation switch is connected to ground provided in the LED-mounted board.

* * * * *